(12) United States Patent
Krinninger et al.

(10) Patent No.: US 11,589,951 B2
(45) Date of Patent: Feb. 28, 2023

(54) INTELLIGENT HOLDING ARM FOR HEAD SURGERY, WITH TOUCH-SENSITIVE OPERATION

(71) Applicant: Brainlab Robotics GmbH, Munich (DE)

(72) Inventors: Maximilian Krinninger, Weßling-Oberpfaffenhofen (DE); Stephan Nowatschin, Munich (DE)

(73) Assignee: Brainlab Robotics GmbH, Munich (DE)

( * ) Notice: Subject to any disclaimer, the term of this patent is extended or adjusted under 35 U.S.C. 154(b) by 447 days.

(21) Appl. No.: 16/559,591

(22) Filed: Sep. 3, 2019

(65) Prior Publication Data

US 2019/0388179 A1   Dec. 26, 2019

Related U.S. Application Data

(63) Continuation of application No. 15/525,585, filed as application No. PCT/EP2015/076446 on Nov. 12, 2015, now Pat. No. 10,426,571.

(30) Foreign Application Priority Data

Nov. 14, 2014  (DE) .......................... 102014016823.9
Nov. 14, 2014  (DE) .......................... 102014016824.7

(51) Int. Cl.
*A61B 90/50*   (2016.01)
*B25J 13/08*   (2006.01)
(Continued)

(52) U.S. Cl.
CPC .......... *A61B 90/50* (2016.02); *A61B 1/00149* (2013.01); *A61B 17/00* (2013.01);
(Continued)

(58) Field of Classification Search
CPC ......... A61B 90/50; A61B 90/37; A61B 90/10; A61B 34/25; A61B 34/30; A61B 34/70;
(Continued)

(56) References Cited

U.S. PATENT DOCUMENTS 7,841,979 B2   11/2010  Hirose
2004/0106916 A1   6/2004  Quaid et al.
(Continued)

FOREIGN PATENT DOCUMENTS

DE          19526915 B4   5/2004
DE      102004050714 A1   4/2006
(Continued)

*Primary Examiner* — Tammie K Marlen
(74) *Attorney, Agent, or Firm* — Blank Rome LLP

(57) ABSTRACT

A holding arm for medical purposes, in particular for holding surgical mechatronic assistance systems and/or surgical instruments, includes a proximal end for attaching the holding arm to a base and a distal end for receiving a surgical mechatronic assistance system and/or surgical instrument; at least one first and one second arm segment, wherein the first arm segment is connected to a first joint and the second arm segment is connected to a second joint, wherein each joint is releasable and lockable. An operating unit is provided for bringing the holding arm into a desired pose, wherein the operating unit is adapted to release the associated joint upon contact between an operator and one of the first and second arm segments. A corresponding method is also provided.

29 Claims, 12 Drawing Sheets

(51) Int. Cl.
  *B25J 19/00* (2006.01)
  *A61B 34/00* (2016.01)
  *A61B 1/00* (2006.01)
  *A61B 34/30* (2016.01)
  *A61B 90/00* (2016.01)
  *A61B 17/00* (2006.01)
  *B25J 19/02* (2006.01)
  *A61B 90/10* (2016.01)
  *A61B 34/20* (2016.01)
  *A61B 90/57* (2016.01)

(52) U.S. Cl.
  CPC .............. *A61B 34/25* (2016.02); *A61B 34/30* (2016.02); *A61B 34/70* (2016.02); *A61B 34/74* (2016.02); *A61B 90/37* (2016.02); *B25J 13/084* (2013.01); *B25J 19/0004* (2013.01); *B25J 19/0008* (2013.01); *B25J 19/023* (2013.01); *A61B 90/10* (2016.02); *A61B 2017/00203* (2013.01); *A61B 2017/00477* (2013.01); *A61B 2034/2048* (2016.02); *A61B 2034/2059* (2016.02); *A61B 2090/066* (2016.02); *A61B 2090/508* (2016.02); *A61B 2090/571* (2016.02)

(58) Field of Classification Search
  CPC ..... A61B 34/74; A61B 1/00149; A61B 17/00; A61B 2034/2048; A61B 2034/2059; A61B 2090/066; A61B 2090/508; A61B 2090/57; A61B 2017/00203; A61B 2017/00477; B25J 13/084; B25J 19/0004; B25J 19/0008; B25J 19/023
  See application file for complete search history.

(56) References Cited

U.S. PATENT DOCUMENTS

| | | |
|---|---|---|
| 2004/0138524 A1 | 7/2004 | Ueda et al. |
| 2005/0075536 A1 | 4/2005 | Otsuka et al. |
| 2005/0209614 A1 | 9/2005 | Fenter et al. |
| 2007/0129846 A1 | 6/2007 | Birkenbach et al. |
| 2010/0163694 A1 | 7/2010 | Fadler et al. |
| 2011/0015647 A1 | 1/2011 | Salisbury, Jr. et al. |
| 2012/0143048 A1 | 6/2012 | Finlay |
| 2012/0223199 A1* | 9/2012 | Abri ............... A61B 90/50 248/282.1 |
| 2017/0007336 A1* | 1/2017 | Tsuboi ............ B25J 9/1674 |

FOREIGN PATENT DOCUMENTS

| | | |
|---|---|---|
| DE | 102011004926 A1 | 9/2012 |
| EP | 1958587 A1 | 8/2008 |

* cited by examiner

INTELLIGENT HOLDING ARM FOR HEAD SURGERY, WITH TOUCH-SENSITIVE OPERATION

CROSS-REFERENCE TO RELATED APPLICATIONS

This application is a continuation of U.S. patent application Ser. No. 15/525,585, filed May 10, 2017, and issued as U.S. Pat. No. 10,426,571 on Oct. 1, 2019, which is a National Stage of International Patent App No. PCT/EP2015/076446, filed Nov. 12, 2015, which claims priority to German Patent App. Nos. DE 102014016824.7 and DE 102014016823.9, both filed Nov. 14, 2014, the disclosures of which are incorporated by reference in their entirety.

FIELD OF THE INVENTION

The invention relates to a holding arm for medical purposes, in particular for holding a surgical mechatronic assistance system and/or a surgical instrument, comprising a proximal end for attaching the holding arm to a base and a distal end for receiving a surgical mechatronic assistance system and/or surgical instrument; at least one first and one second arm segment, wherein the first arm segment is connected to a first joint and the second arm segment is connected to a second joint, wherein each joint is releasable and lockable. The invention also relates to a method for positioning a surgical mechatronic assistance system and/or surgical instrument coupled to a holding arm. The invention further relates to a holding arm for medical purposes, in particular for holding a surgical mechatronic assistance system comprising a proximal end for attaching the holding arm to a base and a distal end for receiving a surgical mechatronic assistance system, and two or more arm segments and two or more joints, by means of which the arm segments are connected to each other by joints, wherein each joint can be released and locked by means of an operating unit. The invention further relates to a method for controlling a mechatronic assistance system, in particular using such a holding arm.

BACKGROUND

Holding arms of the kind initially specified have long been known from the prior art and are specifically used in surgery to relieve an operator of static holding work. Such a holding arm is used to hold a mechatronic assistance system and/or a surgical instrument, for example a manipulator, an endoscope, a surgical clamp or the like. The holding arms initially specified have proved their usefulness for holding endoscopes, in particular. In endoscopic surgery, an operator generally operates an instrument with both hands, while an assistant holds the endoscope in order to make the operating area visible on a screen. Holding the endoscope over a protracted period is very tiring. Holding arms are increasingly used for that reason.

Such a holding arm is known from DE 195 26 915 B4, for example. The holding device for medical purposes disclosed therein has a connection member and a holder for surgical tools, as well as an arm arranged between the holder and the connection member. The arm is connected to the holder and to the connection member, or to an adjacent arm via a joint, and can be coupled to a pneumatically operable device for selectively locking and releasing the joints, wherein the device locks the joints by the action of a mechanical spring which exerts a braking force on the joint, and wherein the device can be pneumatically switched to a joint-releasing mode against the force of that spring. An actuator by means of which a valve can be opened is disposed on the holder at the proximal end of the arm, so that the separate joints of the arm can be adjusted. When the actuator is released, the valve is closed again, thus locking the joints.

A similar holding arm is disclosed in EP 1 958 587 B1. The holding disclosed therein likewise has a plurality of joints, and a touch-sensitive sensor for actuating the joints is provided. The sensor is disposed on the holding arm adjacent to the medical instrument, so that the operator comes into contact with the touch-sensitive sensor on gripping the medical instrument, as a result of which the joints of the holding arm are released.

The holding arm disclosed in DE 195 26 915 B4 and also the one disclosed in EP 1 958 587 B1 is used primarily as a kind of exoskeleton for the operator, so that the operator can rest on the holding arm during the operation and can release all the joints on gripping the medical instrument or when operating the actuator, so that the pose of the holding arm can be altered.

Another holding arm, adapted to hold an endoscope, is known from DE 10 2004 050 714 A1. The arm has a plurality of joints which can be closed pneumatically. The holding arm is connected to a foot-switch valve. When the foot-switch valve is operated, compressed air enters all the joints, thus releasing them.

Another such holding arm is disclosed in DE 10 2011 004 926 A1. The holding arm has a plurality of arm segments and a plurality of joints by means of which the separate arm segments are coupled to each other. The holding arm according to DE 10 2011 004 926 A1 also has a first interface at the proximal end, for coupling the holding arm to a standard rail on an operating table. The first interface is substantially in the form of a clamp. The holding arm also has an interface at the distal end, which is likewise in the form of a clamp and which is used to receive an endoscope. Even though this arm is basically well-suited for purely holding endoscopes, there is nevertheless a need to provide greater versatility in the range of uses for such holding arms, in particular to adapt them to different tasks. It is also desirable that the safety of such holding arms be improved such that the risk is reduced of a patient being injured during an operation in which the holding arm is used.

One disadvantage, however, is that precise positioning of the mechatronic assistance system and/or surgical instrument disposed on the holding arm is difficult to achieve with the holding arm known from the prior art, and is strongly dependent on the skill of the operator. The precision of positioning is confined solely to the skills of the operator who spatially positions the distal end of the arm.

One known way of eliminating this problem is to use robotically assisted holding arms which, in addition to releasable and lockable joints, also have motors in the joints, which can be controlled via a terminal. Precise positioning is possible with these robotically driven holding arms, but a robotic controller of this kind is highly complex and requires extensive training of the operator. Operating such a controller is complicated and may therefore cause problems.

SUMMARY OF THE INVENTION

The object of the present invention is to provide a holding arm of the kind initially specified which is simple and, in particular, intuitive to operate, while simultaneously allowing more precise positioning of the mechatronic assistance system and/or surgical instrument attached to the distal end of the arm.

This object is achieved by a holding arm of the kind initially specified which has an operating unit for bringing the holding arm into a desired pose, the operating unit being adapted to release the associated joint upon contact between an operator and one of the first and second arm segments. According to the invention, therefore, the operating unit is adapted to release the first joint when contact occurs between an operator and the first arm segment and to release the second joint when contact occurs between an operator and the second arm segment. Thus, according to the invention, when an operator comes into contact with a respective arm segment, only the associated joint is released. This makes it possible to move individual joints intuitively and thus to adjust the holding arm segment by segment and to bring it into a desired pose. By this arrangement, positioning can be carried out with greater precision, because each segment can be separately adjusted incrementally. It is likewise possible to contact a plurality of segments at once, with the result that a plurality of joints can be released and thus adjusted simultaneously. This allows the holding arm to be brought into a desired pose in a simple manner, and in particular intuitively.

In addition to the first and second arm segments, further arm segments which are each associated in like manner with a respective joint are preferably provided. The arm segments themselves are substantially rigid and preferably rod-shaped. The expression "rod-shaped" here includes not only substantially straight arm segments, but also slightly or strongly curved arm segments. In such a holding arm, arm segment and joints always alternate, and the holding arm at the distal and at the proximal end can end with a joint or with a segment or with a connection member. The holding arm can be attached to a base with its proximal end. The base may alternatively be coupled securely to the arm, or the arm can be removed from the base. In one embodiment, the base is in the form of an operating table, and the holding arm can be coupled to an operating table. The holding arm can preferably be coupled to a standard rail provided on the operating table. Such standard rails are generally provided on operating tables, so a standard interface can be provided on the holding arm to couple it to the standard rail of an operating table. Normal operating tables are also assembled from separate segments. For coupling purposes, the segments have matching, generally manufacturer-specific coupling points on their front sides. The holding arm can preferably to attached to the operating table via such a coupling point. A manufacturer-specific adapter may be provided for that purpose at the proximal end. Alternatively, the base is provided as a separate apparatus, for example a stand which can be set up on the floor of an operating theatre. In another alternative, the base is configured as a holder which can be attached to a wall or ceiling of an operating theatre, for example.

The holding arm is preferably configured as a passive holding arm, so called, and for that reason has joints which are actively braked exclusively, but not driven joints as is often the case with robotic holding arms. Each joint is therefore releasable and lockable only, but cannot be driven. As a result, the holding arm is simple in design and does not need a complex controller in order to operate it.

According to a first preferred embodiment of the invention, the operating unit has contacting devices which are adapted so that an operator comes into contact with them, wherein a first contacting device of the operating unit is arranged on the first arm segment and a second contacting device is arranged on the second arm segment. When contact is made with the first contacting device, the first joint is preferably released, and when contact is made with the second contacting device, the second joint is preferably released. The contacting devices are used to detect contact between the user and the arm segment. The contacting devices are preferably arranged on a surface of the respective arm segment. The contacting devices may extend over the entire arm segment or may occupy only a section of it. Each contacting device preferably extends around approximately half the circumference about a central axis of an arm segment. As a result, the contacting devices can be easily reached in every pose of the holding arm, and an operator can easily come into contact with it.

According to another preferred embodiment, each contacting device has two contact elements arranged substantially opposite one another on the arm segment. According to this embodiment, it is preferred that the associated joint is released only when there is contact with both the contact elements. The contacting device preferably consists of the two contact elements, so there is contact with the contacting device only when both contact elements are contacted by the operator. By arranging the two contact elements substantially opposite each other, preferably in relation to a plane containing a central axis of the arm segment, it is possible to distinguish between inadvertent contact, for example by an arm of an operator, from intentional contact, namely deliberate gripping of the arm segment, so according to this embodiment the joint is released only when the arm segment is gripped, in particular by the operator's hand, in which case the two opposite sides of the arm segment are contacted. In order to operate the holding arm and to bring the holding arm into a desired pose by means of the operating unit, the arm segment must therefore be gripped by the operator in such a way that he comes into contact with both the contact elements of the contacting devices, whereupon the associated joint is released by the operating unit and the arm segment can be moved.

According to one preferred development of the invention, the contact elements are provided in the form of pushbuttons. Pushbuttons are particularly simple elements which can not only be detected visually by the operator, but also provide direct tactile feedback when the button is pressed. Such a pushbutton may be provided in the form of a simple closing contact of an electrical circuit, for example, or as a capacitive switch. As long as both the pushbuttons according to this embodiment are pressed, the joint associated with the respective arm segment is released; as soon as the operator releases both or even just one of the two pushbuttons, the joint is locked again by the operating unit.

According to one preferred alternative embodiment, the contact elements are provided in the form of touch-sensitive sensors. The sensors are preferably substantially planar in shape and extend over a substantial portion of the surface of the respective arm segment. The sensors are preferably provided in the form of pressure-sensitive sensors, capacitive sensors, heat-sensitive sensors and/or as optical sensors. Such sensors have the advantage that they can cover a larger area, which leads to the result that the operator does not have to contact the arm segment quite as exactly, but that it is sufficient if the operator's grip is substantially around the arm segment and thus comes into contact with the sensor or sensors.

In another preferred embodiment, the operating unit is designed to release the associated joint according to the intensity of contact. What is meant by intensity here is a pressure and/or force which is applied by the operator. It is possible in this way for the operator to control a degree of freedom with the force that he applies when gripping. It is thus conceivable and preferred that the associated joint is only partially released when the intensity of contact is low, so that the arm segment can be moved only slowly and against a resistance. Whenever the intensity is high and thus when the grip is strong, the joint is opened completely, so the arm segment can be moved with substantially no resistance. The joint can also be partially release by releasing it intermittently in different frequencies.

In another preferred embodiment, the operating unit has a display for indicating contact between an operator and the arm segment. The display is preferably adapted to emit a tactile, visual and/or audio signal. Thus, according to this embodiment, when there is contact between the operator and the arm segment, not only is the associated joint released, but a signal is emitted simultaneously as feedback for the operator, in particular a tactile, visual and/or an audio signal. It is preferred, for example, that contact elements of contacting unit have a lighting device, such as an LED or the like, which lights up when contact occurs between the operator and the contact element. A tactile signal includes a vibration, for example. An audio signal may be a simple sound or may also include voice output such as "joint released".

In another preferred configuration, the operating unit further includes a switch for releasing all the joints. Such a switch, by use of which all the joints can be released, can be called a master switch. It may be designed as disclosed, for example, in EP 1 958 587 B1, i.e. as a switch at the distal end of the holding arm, or as a footswitch which is disposed at a distance from the holding arm, as disclosed in DE 195 26 915 B4. Such a switch which acts as a master switch is advantageous for rough positioning of the holding arm, for example at the beginning of the operation procedure. It is then possible to release all the joints simultaneously and to preposition the holding arm roughly before subsequently locking all the joints again by letting go of the switch and, in order to obtain a desired pose, to adjust individual arm segments by contacting those arm segments only. It is preferred that the switch has two different switch positions, the joints being released in a first switch position in such a way that a tool center point of a mechatronic assistance system and/or surgical instrument attached to the holding arm can be rotated, and that the joints can be released in a second position of the switch in such a way that the tool center point can be moved translationally in three spatial directions. In this way, the holding arm can be roughly positioned in a particularly preferred manner.

In one preferred embodiment of the invention, the first joint is disposed at a proximal end of the first arm segment and the second joint is disposed at a proximal end of the second arm segment. Each segment has a proximal and a distal end, the proximal end of the arm segment being the end which, in the direction of the arm, is proximal to the proximal end of the holding arm, and the distal end of the arm segment is the end that is oriented to the distal end along the holding arm. Thus, according to this embodiment, the first joint is located between the first arm segment and the proximal end of the holding arm, so the first arm segment can be moved when there is contact with the first arm segment. The same applies accordingly to the second arm segment and the second joint. The holding arm can be operated in a particularly intuitive manner with this variant, because the arm segment which the operator contacts is the one that can always be moved.

In one preferred alternative, when contact occurs between the operator and both the first and the second arm segment, the operating unit releases all the joints disposed between said arm segments. If the operator grips two arm segments of a holding arm according to this embodiment, which are adjacent to or distanced from each other, all the joints (one or more joints) located between those arm segments are released as a consequence. By gripping two arm segments, the operator is thus able to move the distal arm segment substantially freely in relation to the proximal of the two arm segments. He can also release all the joints of the holding arm, namely whenever he grips both the distal and the proximal arm segment. By this provision, one or more joints can be released in a simple and intuitive manner.

In another preferred embodiment of the invention, the joints have brakes by use of which the joints can be released and locked. The holding arm is preferably in the form of a passive holding arm. The purpose of the brakes is to brake or prevent movement of the arm segments relative to each other, i.e. to brake or prevent any movement of the joints. If the brakes are released, the joints are released.

In an idle state, the brakes are preferably biased in such a way that the joints are locked. When the holding arm is in an idle state, it is therefore in a locked state, thus improving the safety of the holding arm when used in the medical field. For example, if the power supply fails due to a malfunction, the holding arm is in a locked state, and the pose of the holding arm remains the same. The energy consumption of the holding arm is also reduced by providing such a bias.

It is particularly preferred that the brakes are designed as electromagnetic brakes and that they each comprise a permanent magnet which biases the brake into the locked state when no current is being supplied. This brake design is particularly useful. In order to release the brakes, they have to be supplied with electrical current so that a braking member is released against the force of the permanent magnet. In the event of a power supply failure, the brake closes again due to the permanent magnet, with the result that the joint is then in the locked state. Compared to spring-loaded brakes, electromagnetic brakes have the advantage that they can exert a strong holding or torque force relative to their weight.

According to another preferred embodiment, the holding arm has six degrees of freedom. It is particularly preferred that the holding arm has seven degrees of freedom. Whereas six degrees of freedom are sufficient to reach any point in space, it is possible with seven degrees of freedom to reach any point with different poses, so the holding arm can always be oriented in such a way that the operating area is easily accessible, for example. For that reason, it is particularly preferred that the holding arm has seven degrees of freedom.

According to one preferred embodiment, the holding arm has seven arm segments and seven joints, with each arm segment being assigned one joint. According to this embodiment, each joint preferably has one degree of freedom, so the holding arm has a total of seven degrees of freedom. It is also possible that each joint has two or more degrees of freedom, with joints having one degree of freedom being preferable on account of their stability. All the joints are preferably designed as rotary joints. It is preferable that some of the joints are designed as rotary joints and some as translational joints. When the joints are all designed as rotary joints, they are preferably disposed in the holding arm in such a way that axes of successive joints along the holding arm, from the proximal to the distal end of the holding arm, are perpendicular to each other.

According to another preferred embodiment, the holding arm has a weight compensation unit for at least partially supporting the weight of one or more arm segments of the holding arm when one or more joints are released. For example, if one joint near the proximal end of the holding arm is released, the operator has to manually hold the entire weight of the rest of the holding arm to the distal end. To prevent the holding arm from sagging after joints are released, a weight compensation unit is preferably provided that compensates the respective weight at least partially. By this arrangement, only a small amount of weight needs to be supported following release by the operator, further simplifying handling as a result.

In one preferred embodiment, the weight compensation unit has a gas spring element which is coupled to at least two arm segments. Such a gas spring element is a simple way of providing a weight compensation unit. The gas spring element is preferably coupled to the two arm segments disposed at the proximal end of the holding arm. Those two arm segments are preferably connected to a joint whose pivot axis is perpendicular to a longitudinal extension of the arm segments. This provides a particularly useful arrangement of the gas spring element, and any forces acting on the holding arm can be supported in an advantageous manner.

It is also preferred that the weight compensation unit has at least one spring element, in particular a torque-producing spring such as a helical spring or a torsion bar, in at least one joint. According, one or more spring elements may be provided in the joints, in addition to, or as an alternative to the gas spring element. A helical spring is provided in a rotary joint, for example, and applies a torque on the joint in such a way that a section of the holding arm is supported when the joint is released. Such helical springs are another simply way of providing weight compensation.

In another preferred embodiment, orientation indicators showing a basic pose of the holding arm are arranged on the arm segments. This is particularly preferred when spring elements are provided in the joints for weight compensation. Due to orientation indicators being provided, it is always easy for a user to see whether a holding arm is in a basic pose or in some different kind of pose. In this way, it is possible to prevent that when a joint is release, a weight compensation unit results in the weight compensation unit biasing the holding arm in the direction of movement and failing to compensate for the weight, but increasing it even further instead. As an alternative, an inner side of the holding arm, or a side of the holding arm that in normal operation is oriented towards the operating area, is designed in a first color, for example, whereas a side of the holding arm facing outwards or away from the operating area is designed in a second color. Alternatively, projections, lettering or the like, which serve as orientation indicators, are provided.

It is also preferred that at least one cable duct is provided inside the arm segments to guide cables from the proximal to the distal end of the holding arm. Such cables, for example for supplying an electrical voltage, or compressed air, or for transmitting light, and the like, are preferably guided inside the holding arm so that no cables which could cause complications during operation run outside the holding arm.

In another preferred embodiment, the first arm segment, relative to the proximal end of the holding arm, has a first mechanical coupling for releasably coupling the holding arm to a second corresponding coupling of an operating table. By this arrangement, the holding arm can be easily coupled to an operating table, in particular to the standard rail.

It is also preferred that the last arm segment at the distal end of the holding arm has a mechatronic interface for coupling the surgical mechatronic assistance system and/or the surgical Instrument to the holding arm. Such a mechatronic interface preferably has a mechanical coupling for holding the assistance system and/or the surgical instrument mechanically, and electronic interfaces for transmitting electrical energy and/or data or signals to the mechatronic assistance system.

In the case of a holding arm of the kind initially specified, in particular a holding arm for medical purposes, in particular for holding a surgical mechatronic assistance system, comprising a proximal end for attaching the holding arm to a base and a distal end for receiving a surgical mechatronic assistance system, and two or more arm segments and two or more joints by use of which the arm segments are connected to each other by joints, each joint being releasable and lockable by use of an operating unit, the objective of the invention is also achieved by a first interface at the proximal end for connecting the holding arm to an energy source and to an external control unit for transmitting signals to and from the holding arm; a second interface at the distal end for coupling the holding arm to the assistance system to control the assistance system; and a transmission unit which is arranged inside the holding arm and which connects the first interface to the second interface in order to transmit energy and signals between the interfaces.

Assistance systems within the meaning of the invention are understood to be any kind of mechatronic manipulators which are used in surgery, such as endoscopes, exoscopes, laparoscopes, trocars and the like. The second interface at the distal end of the holding arm is designed to couple mechanically with the assistance system in order to hold the latter in a defined position relative to the holding arm, and also to provide the other connections that are necessary, such as a connection for electrical energy and a connection for transferring signals, in particular control signals. A transmission unit, which preferably has a bus system, is provided inside the holding arm. The transmission unit also has means for transmitting electrical energy. Any cables that are required in order to transmit electrical energy and/or data from the first interface to the second interface are thus arranged inside the holding arm arranged and are thus protected during operation of the holding arm. At the first interface, couplings are also provided for coupling the holding arm to an energy source and to an external control unit, such as a computer and/or an OP system. This provides the holding arm with a greater range of possible applications, and allows it to be used in a versatile manner for different assistance systems. Safety is improved at the same time, because it is not necessary to attach additional cables or the like. Instead, the assistance system need only be connected to the second interface at the distal end, and the holding arm itself only has to be coupleable via the first interface at the proximal end to an energy source and an external control unit.

A particularly preferred embodiment is one in which the first interface has a connector for an external accumulator. This makes the holding arm independent from a stationary power supply and results in the fact that cables can still be avoided. This also means that, in the event of a power failure, the holding arm remains operational, thus improving safety. The first interface preferably has a connection for connecting the holding arm to a navigation apparatus, in particular an OP navigation apparatus. In modern-day operating theatres, a plurality of robotic systems are used in most cases. Due to the holding arm being connected to such a navigation system, it is possible that the latter transfers and receives position data, thus making it possible to prevent any collision with other robotic systems. The first interface preferably has a Bluetooth®, a USB, an RS-232, and/or an optical connector as well. By use of a Bluetooth® connection, it is possible, for example, to transfer signals to the holding arm and to provide these via the transmission unit to the second interface, where they are then transferred to a surgical mechatronic assistance system, such as a manipulator. The same applies for USB and RS-232 interfaces. USB and RS-232 interfaces are particularly suitable for connecting conventional PCs or OP systems to the holding arm.

In another preferred embodiment, the first interface has a connector for an X-ray machine, a medical ultrasonic scanner or a medical laser device, and the transmission unit is configured to transmit X-Rays, ultrasonic signals and/or a medical laser beam, and the second interface is configured to emit X-Rays, ultrasonic signals and/or laser beams onto an operating area, or to provide X-Rays, ultrasonic signals and/or laser beams to a surgical mechatronic assistance system. It is also possible by this means to deploy the holding arm is a versatile manner, and cabling in the operating area can be largely avoided. X-ray machines, ultrasonic scanners and medical lasers may be arranged distally from the patient and transferred and provided to the operating area by means of the holding arm.

In another preferred embodiment, the holding arm has an orientation sensor in at least one joint, for detecting an attitude of the joint. An orientation sensor for detecting the attitude of a joint is preferably disposed in every joint. Such an orientation sensor may be in the form of a capacitive displacement sensor, for example, which mechanically senses a path of joint movement and in that way determines an angular position, or in the form of an acceleration sensor which detects spatial movement of the joint. In addition or alternatively thereto, motion sensors are provided in the arm segments so that the spatial position of the arm segments can be determined. By this arrangement, it is possible to define a holding arm pose which can then be provided to the assistance system and/or to the external control unit via the first and/or second interface. This is particularly advantageous when an OP navigation system is used and the latter uses the information about the pose of the holding arm in order to coordinate navigation. It is also possible to determine, via the pose of the holding arm, whether a collision with other devices or with the holding arm itself is liable to occur. The safety of the holding arm is further improved as a result.

If an acceleration sensor is used as the orientation sensor, it is also possible to detect movement of the holding arm as a whole, without changing the pose. For example, if the operating table moves during the operation, the holding arm can detect that movement. The holding arm may be adapted to emit a warning signal when the operating table reaches a particular inclination, for example from 15 degrees onwards. If an inclination of the operating table is set too steeply, it is possible that a patient on the operating table will slide along the operating table, and that may cause injuries. For example, if an endoscope which is introduced into a patient's nose, for example, is disposed at the distal interface of the holding arm, and if the inclination of the table is then adjusted, the holding arm detects the inclination of the table by use of the motion sensors, and also, by use of torque sensors in the joints, any change in the load acting on the endoscope, which may likewise be an indication that the patient on the operating table is sliding. The holding arm is preferably adapted to emit a signal, for example a warning sound, when predetermined threshold values are exceeded. The holding arm may also be configured to emit a signal, for example to an OP system or directly to an operating table, when the holding arm is coupled through the proximal interface to an OP system or to the operating table, such that any movement of the table is blocked when an endoscope disposed at the distal interface is in situ. It may also be arranged that it is no longer permitted, after patient movement or table movement relative to the holding arm is detected, to move to a previously adopted position of an assistance system, in particular of an endoscope, relative to the patient. Injuries can be prevented in that way also.

If an OP navigation system is additionally present, it is also possible by means of the holding arm according to the invention to integrate unnavigated instruments, which do not have any localisers associated with the navigation system, into the navigation system via the holding arm. By use of the holding arm, it is possible to determine the position of an unnavigated instrument disposed at the distal interface of the holding arm. To achieve that purpose, a localiser is disposed on the holding arm or at the base to which the holding arm is coupled, so that the position of the holding arm within the navigation system is known. The holding arm may transfer data representing the position of the instrument to the navigation system via the proximal interface, and the navigation system can process the data and in that way integrate the unnavigated instrument into navigation. In addition to acceleration sensors, other position and gyro sensors are also preferred. By holding instruments, by use of the holding arm, which do not have any sensors or the like of their own (such as surgical clamps and the like), the position of those instruments relative to the table is known. In many cases, operating tables consist of separate segments which can be manually adjusted. A head plate, for example, may be raised, tilted or moved back and forth. The relative position of the patient to instruments often changes as a result, and injuries may be caused as a result. Due to the holding arm having orientation sensors, it can detect any movement of the operating table or segments of the operating table and can thus warn of any movement of the patient relative to the assistance system (for example, to the surgical clamp), by emitting a signal when such a relative movement is detected. It is also possible that the holding arm can transfer data about its pose to other systems via the proximal interface, for example to C-arms (for example, the Artis zeego system made by Siemens AG, Erlangen, Germany), which means that collisions can be prevented.

In another preferred embodiment, a torque sensor is disposed in at least one joint to detect a torque acting on said joint. Such a torque sensor is preferably disposed in all the joints. By detecting the torques acting on the joints, it is possible to determine a force that is acting at the distal end of the holding arm. In that way, it is possible to determine the weight of an assistance system which is coupled to the distal end. It is also possible when using the holding arm to determine forces acting upon it. It is conceivable, for example, that an endoscope is disposed at the second interface. When handling the endoscope, for example when introducing the endoscope into a body orifice of a patient, it is possible to determine a resistance encountered by the endoscope. It is possible in that way to identify whether there is any risk of the patient being injured. Safety is further improved as a consequence. The torque data that are captured are preferably provided at the first and/or second interface. This allows the torque data to be processed at the external control unit, and the latter may emit a warning signal or the like, for example in the aforementioned case of a collision between an endoscope and a resistance in the body of a patient.

By provision of the torque sensors, it is also possible to determine a weight of an assistance system disposed at the distal interface. The holding arm is preferably designed in such a way that it blocks poses in which a particular torque threshold of a joint would be exceeded due to the weight of an assistance system. For example, if a relatively heavy endoscope is disposed at the distal end of the holding arm, a pose in which the holding arm would project very far from the base, thus producing a very high torque in a proximal pivot joint, is blocked. An operator cannot move the holding arm into such a pose, because brakes in the joints prevent the holding arm beforehand from being moved into such a pose. The safety of the holding arm is further improved by this arrangement. It is also conceivable that the weight of the assistance system is not determined by the holding arm, but that the assistance system transmits its own weight to the second interface at the distal end, and that the data representing that weight are stored and processed accordingly by the holding arm. Additionally or alternatively, it is preferable that a warning sound is emitted when certain threshold values are exceeded. It is also preferred that lighting device which light up when a predetermined threshold value for a joint is exceeded are provided at the joints. If too high a torque is acting on a joint, a lighting device at that joint is activated and an operator can perceive in that way which joint needs less load on it, in order to achieve a stable pose.

The first and/or second interface preferably have transmission units for transmitting the data captured by the sensor or sensors. These transmission units preferably include the interfaces initially specified, such as Bluetooth®, USB, RS-232 or similar.

According to another preferred embodiment, the holding arm comprises a recognition unit for recognizing an assistance system coupled to the second interface, wherein the operating unit is adapted to release or to lock the joints according to the assistance system coupled to the second interface. Such a recognition unit preferably has a barcode scanner, a QR code scanner or an RFID scanner. An assistance system coupled to the second interface is preferably provided with a respective barcode, QR code or an RFID chip containing an identifier for the assistance system and preferably information about said system. By this means, the holding arm is able to recognize which assistance system is coupled to the second interface coupled and is thus able to partially or completely prevent the release of certain joints. An endoscope, for example, is disposed at the second interface. The RFID chip of the endoscope contains information about said endoscope, such as the geometrical dimensions of the endoscope. This information is recognized by the recognition unit and is passed on to the operating unit of the holding arm and/or to the external control unit. The operating unit is configured to prevent such poses of the holding arm in which the endoscope would collide with the holding arm. The operating unit may also be additionally configured to prevent such positions of the holding arm, in which the endoscope collides, for example, with an operating table or other objects.

It is preferable that the recognition unit also be adapted to recognize an instrument which is introduced into the operating area and to provide data representing said instrument at the first interface. The recognition unit is also preferably adapted to recognize an instrument which is removed from the operating area and to provide data representing said instrument at the first interface. For that purpose, the instrument preferably has a transmitter, for example an RFID chip, which communicates by implementation of an appropriate receiver, for example an RFID sensor, which is provided in the recognition unit. In this way, it is possible to determine at which moment which instrument is introduced into the operating area, and whether said instrument has left the operating area again. For example, if it is established at the end of an operation procedure that seven instruments were brought into the operating area, but that only six were removed from it, then this can be an indication that an instrument is still in the operating area, with the result that the patient may be put at risk.

According to another preferred embodiment, the holding arm has a camera which is preferably disposed at the distal end, wherein the camera is provided to observe an operating area and is coupled to the first interface to transfer image data at the first interface. The operating area can thus be monitored in an advantageous manner. The camera is disposed particularly close to the operating area by the coupling on the holding arm and has a "clear view" over the operating area. Its position can also be adjusted by means of the holding arm. The camera can also be used to monitor objects, such as other surgical instruments and the like in the vicinity of the holding arm and thus to prevent any collision with them. For example, if the camera perceives that the holding arm is being brought too close to an instrument located in the operating area, the operating unit can be designed to lock one or more joints to prevent a collision. In such a case, it is preferable that the operating unit has a controller on which image recognition software designed for that purpose is installed. The camera may be integrated in the holding arm itself and be securely connected to it, or the camera is part of an exoscope which is coupled to the second interface. The camera is preferably configured as a Full HD camera or as a 3D camera. If the camera is part of an exoscope, the latter is connected to the second interface at a voltage interface, a fiber optic interface and a data interface. When in use, the camera of an exoscope is typically disposed approximately 25 cm to 75 cm away from an operating area. Due to the camera of the exoscope being coupled directly to the distal interface, data can be transmitted at the proximal interface, for example, to an OP system. Images recorded by use of the camera can now be viewed by a user via an appropriate 2D or 3D monitor of the OP system. Since it is possible to position the camera or the lens of the camera relatively close to the operating area by use of the holding arm, powerful magnifications, by a factor of 12, for example, can be easily achieved using appropriate monitors. This results in the fact that it is no longer necessary to deploy a large, unwieldy operating microscope, because the holding arm, which is equipped with a camera or an exoscope, is sufficient for watching the operating area. Due to the holding arm having additional sensors for detecting the pose of the holding arm, the position from which the images are recorded by the camera, or the camera of the exoscope, is also known when the holding arm according to the invention is used. The recorded image data can thus be associated with chronological position information. It is thus possible, after the operation has been completed, to associate a viewing angle and a viewing position to each single image. It is then possible to draw conclusions from the documentation postoperatively about which operating strategy was chosen and from which perspective.

It is preferable that the holding arm also has a microphone which is coupled to the controller and/or the operating unit, and the controller and/or the operating unit has appropriate speech recognition software so that audio signals received by the microphone can be converted into adjustment and control signals for the holding arm. Thus it is preferable, when receiving a respective audio signal via the microphone to control a camera disposed on or integrated in the holding arm in such a way that the camera records a still picture or so-called snapshot and transfer it to the second interface on the holding arm so that data representing said snapshot can be transferred into a system at the first interface of the holding arm. In this way, it is possible for the operator to give a command during the operation to take a snapshot, for example by speaking the word "snapshot" and with a signal then being sent from the controller to the camera by use of speech recognition software provided in the controller, and for data representing that snapshot to be provided at the second interface. Position data for such snapshots can also be transferred by the holding arm.

If there is also a navigation system in an operating theatre in which the holding arm is being used, the holding arm can be connected to that navigation system via the first interface. Such navigation systems are obtainable from Karl Storz GmbH & Co. KG, Tuttlingen, Germany, for example, or also from Olympus Deutschland GmbH, Hamburg, Germany. In such a case, an optical localiser which interacts with the navigation system is preferably secured to the base of the holding arm. The navigation camera of the navigation system thus detects the holding arm and also the operating area. The patient, too, is fitted with localisers so that it is possible for the navigation system to detect the spatial position of a patient. However, the defined workspaces of a navigation system are generally limited. If a camera or an exoscope is now provided on the holding arm, it is also possible to position the camera and the exoscope outside the workspace of the navigation system and to determine the position of the camera and of the exoscope by means of the holding arm. This allows the limited workspace of the navigation system to be kept free of additional tools, and the navigation system to be put to better use. Position data for the camera can also be stored along with the data representing the recorded images, and linked to data from the navigation system. In another preferred embodiment, a safety element is provided at the second interface and is coupled to the operating unit in such a way that the operating unit locks all the joints when the safety element indicates a faulty link between the assistance system and the second interface. Such a safety element may be in the form of an electronic safety element or in the form of a mechanical safety element. The safety element can be designed, for example, such that an electric circuit is closed when the assistance system is correctly coupled to the second interface. In one alternative embodiment, a magnet is disposed on the assistance system, and the second interface has a matching sensor which is adapted to detect the magnetic field of the sensor disposed on the assistance system. Other alternatives are conceivable here. The safety of the holding arm is further improved in this way also. If an assistance system is not coupled correctly to the second interface, all the joints are locked, and the holding arm cannot be moved. In this way, it is possible to reduce the risk of a holding arm being used during an operation with an assistance system that is not correctly coupled.

In a third aspect of the invention, the object referred to at the outset is achieved by a method for positioning a surgical mechatronic assistance system and/or surgical instrument coupled to a holding arm, preferably the holding arm according to any one of the preferred embodiments of a holding arm according to the first or the second aspect, as described in the foregoing, the holding arm having at least six degrees of freedom, said method comprising the steps of: holding a pose of the holding arm; detecting operator contact with a first arm segment of the holding arm; releasing a first joint associated with the first arm segment, as long as said contact is detected, and locking the first joint as soon as contact is no longer detected. With such a method according to the invention, a method is provided for positioning an assistance system and/or a surgical instrument coupled to a holding arm, allowing the operator to position the assistance system and/or surgical instrument intuitively and simply.

In an idle state, the pose of the holding arm is preferably held. Not until contact is detected between an operator and a first arm segment is the associated first joint released for as long as contact is detected. When contact stops, the joints is locked. By this provision, the joint is released for as long as there is contact between the operator and the arm segment, so that by contact the arm segment the operator is able to move that arm segment and adjoining arm segments in order to spatially position the assistance system and/or the surgical instrument. This kind of positioning is intuitive, with the result that the safety of a surgical operation using such a holding arm is also improved, in that operating errors can be avoided. The method is preferably performed in the field of head surgery. The method preferably comprises the step of holding an endoscope during head surgery. Precise positioning is essential in the field of head surgery, in particular, because there is limited space for manipulating tissue and because tissue is highly sensitive to manipulation, depending on position.

It is preferred that the method also comprises the steps of: detecting operator contact with a second arm segment of the holding arm; releasing a second joint associated with the second arm segment, as long as said contact is detected, and locking the second joint as soon as contact is no longer detected. The steps are preferably carried out simultaneously or after the steps described above. It is possible and preferred that an operator contacts only one arm segment or two or more arm segments. For that reason, all the joints associated with the respective arm segments being contacted are released. In this way, it is possible for the assistance system and/or the surgical instrument to be positioned in a particularly simple and rapid manner.

In one preferred development of the invention, contact is detected on two substantially opposite sides of the arm segment. It is possible in this way to distinguish between inadvertent contact and intentional gripping, and in this way to preclude any inadvertent contact in which the operator touches an arm segment with just one arm or with the back of his hand, for example, without deliberately wanting to make such contact. Only when contact is detected on two opposite sides, which is generally what happens when the respective arm segment is gripped, is the associated joint released.

According to another preferred embodiment of the method, an intensity of contact is detected and the joint is partially or fully released depending on said intensity. It is preferable that the joint is partially to completely released in an infinitely variable manner, depending on the intensity of contact. For example, if an operator grips the respective arm segment only lightly and applies only a small force in doing so, the joint is only partially released in such a way that the joint can be moved against a resistance. If, in contrast, the arm segment is firmly gripped and a strong force is applied in doing so, the joint is completely released, so the arm segment can be moved with substantially no resistance. This also allows intuitive operation, and an operator is able to control how the joints are released by varying the force he applies when gripping. By briefly tapping the arm segment, for example, it is possible to release the joint only briefly, thus allowing the arm to be finely positioned.

The method preferably includes the additional step of outputting a signal for displaying contact between the operator and the arm segment. By performing this step, the operator receives direct feedback about contact and thus about the associated joint being released.

It should be understood that the holding arm according to the first aspect of the invention and the method according to the third aspect of the invention have identical and similar aspects as specified, in particular, in the dependent claims. Reference is therefore made to the entire description above in respect of the holding arm for the preferred variants of the method and their respective advantages.

In a fourth aspect of the invention, the object specified at the outset is achieved by a method for controlling a mechatronic assistance system coupled to a holding arm, in particular using a holding arm according to one of the preferred embodiments as described in the foregoing, in order to navigate said system during surgical treatment, said method comprising the steps of: coupling a mechatronic assistance system to a second interface of the holding arm at its distal end; transmitting electrical energy and signals from a first interface of the holding arm to its proximal end, wherein transmission is carried out by use of a transmission unit which is arranged inside the holding arm and which connects the first interface to the second interface in order to transmit energy and signals between the interfaces.

Applying such a method for controlling a mechatronic assistance system coupled to a holding arm specifically improves the safety of a holding arm in use and the safety of surgical steps carried out with the holding arm.

The method preferably comprises the additional steps of: detecting attitudes of joints of the holding arm; determining a pose of the holding arm using the detected attitudes of the joints, and providing data representing the determined pose at the first interface. The data provided at the first interface are preferably by transferred by means of the latter to an external control unit in which the data are processed and/or analyzed. Such an external control unit may take the form of a common PC, for example, or an OP system.

It is also preferred that the method comprises the steps of: detecting torques acting on joints of the holding arm; determining a force acting at the distal end of the holding arm, and providing data at the first interface which represent the determined force. These data, too, are preferably transferred to an external control unit. The external control unit can process and/or analyze those data. For example, the external control unit may emit a signal when a threshold value for a force acting on the holding arm is exceeded.

In another preferred embodiment, the method comprises the steps of: recognizing an assistance system coupled to the second interface; releasing and locking joints of the holding arm according to the recognized assistance system; providing data at the first interface which represent the recognized assistance system. Performing these steps further improves the safety of the holding arm and the use of the holding arm in a surgical procedure. As soon as a critical and/or "impermissible" pose is reached with the holding arm, or the holding arm is moved into such a pose, respective joints are locked so that this critical or "impermissible" pose cannot be reached. The safety of the holding arm is further improved by this means.

It is preferred that the method also comprises the steps of: recognizing, using a recognition unit, an instrument which is introduced into an operating area; providing data at the proximal interface which represent the instrument and indicate that the instrument has been introduced into the operating area. According to these steps, instruments which are not coupled to the distal end of the holding arm are recognized by using the recognition unit. For that purpose, the recognition unit preferably has a receiver, for example an RFID sensor, while the instrument or instruments brought into the operating area have a transmitter, for example an RFID tag. It is also possible that the holding arm has a near-field sensor, and that the instrument has a near-field chip. Other kinds of transmitter and receiver are also possible. Thus, whenever an instrument is introduced into the operating area, this is detected by performing this method. Data representing the instrument and indicating which instrument is involved are provided at the first interface, as are data indicating that the instrument has been introduced into the operating area. These data are preferably stored.

In one preferred development of the invention, the method also comprises the steps of: recognizing, by use of a recognition unit, an instrument which is removed from an operating area; providing data to the first interface which represent the instrument and indicate that the instrument has been removed from the operating area. The above description applies here accordingly. However, what is detected here, according to these steps, is whether and when the respective instrument has been removed from the operating area. If, after completing the operation, there is a discrepancy between the instruments introduced and those removed from the operating area, this is an indication that there are still instruments in the operating area. In this way, any risk during the operation can be reduced.

In one preferred embodiment, the method comprises the steps of: detecting image data of an operating area, and providing the image data at the first interface. The image data include not only two-dimensional but also three-dimensional image data and are preferably captured by a camera which is disposed at the distal end of the holding arm.

In one preferred development of the invention, the image data are linked to position data of the assistance system. The assistance system preferably has a camera. Due to the image data being linked to position data of the assistance system, and in particular due to image meta data containing data about the position of the camera, it is possible to determine the position from which the respective picture was taken.

In one preferred embodiment of the method, the method comprises the steps of: detecting an audio signal using a microphone; detecting a voice command in the audio signal; converting the voice command into a control signal for the assistance system, and providing the control signal at the second interface. A well-known speech recognition software is preferably used to process the audio signal. Specific voice commands may be associated with specific control signals. For example, it is possible that a "screenshot" voice command is associated with a control signal which causes a camera disposed at the second interface to take a picture. Other control signals are conceivable and preferred.

It is preferred that the method further comprises the steps of: determining whether the assistance system is correctly coupled to the second interface; locking all the joints of the holding arm if the assistance system is not correctly coupled to the second interface. Safety is further improved by this development also. In addition, the method may comprise the step of outputting an alarm signal if the assistance system is not correctly coupled to the second interface. Such an alarm signal may take the form of an audio signal or a visual signal, for example.

In one preferred embodiment of the method, said method comprises the additional step of displaying a representation of data transferred at the first and/or second interface. Such representation may include, for example, displaying an identifier of an assistance system which is disposed at the distal end. It is possible to display information about that assistance system, such as its capabilities, restrictions, adjustment parameters, and the like. It is also possible to display a pose of the holding arm, or forces acting on individual joints.

In another preferred embodiment, the method comprises the steps of: storing the data provided at the first interface; producing an operation log using the stored data. It is preferable that all the data captured and provided are stored, and that the operation log is produced on the basis of those data. The captured data include data relating to the position and attitude of the joints, and to forces acting on the distal end. On the basis of these data, it is possible to trace every single pose of the holding arm during an operation and thus to know the spatial location, throughout the operation procedure, of an assistance system which is disposed on the holding arm. It is then possible to trace how the assistance system was moved relative to the patient and thus to trace the steps that were performed. This means that, according to this aspect of the invention, it is not necessary for an operator to keep a record of every single step performed. This can be done afterwards by retrieving and processing these data. This also improves safety, because the risk of record-keeping errors is reduced.

It is also preferred that the method comprises the steps of: storing all the data provided at the first interface, and generating a DICOM file on the basis of the stored data. A DICOM file is a well-known data exchange format for OP systems and can be used by many different systems in order to analyze and follow-up on an operation afterwards. A DICOM file can also be used for storage of data in an electronic patient file. These steps are preferably performed automatically after an operation procedure has been completed.

It should be understood that the holding arm according to the second aspect of the invention and the method according to the fourth aspect of the invention have identical and similar sub-aspects, as specified, in particular, in the dependent claims. In that regard, reference is made to the entire description above, regarding the first aspect of the invention, for specific embodiments of the holding arm and for the advantages of the method.

BRIEF DESCRIPTION OF THE DRAWINGS

The invention shall now be described in more detail with reference to one embodiment and with reference to the attached drawings, in which.

DETAILED DESCRIPTION

Figure 1:
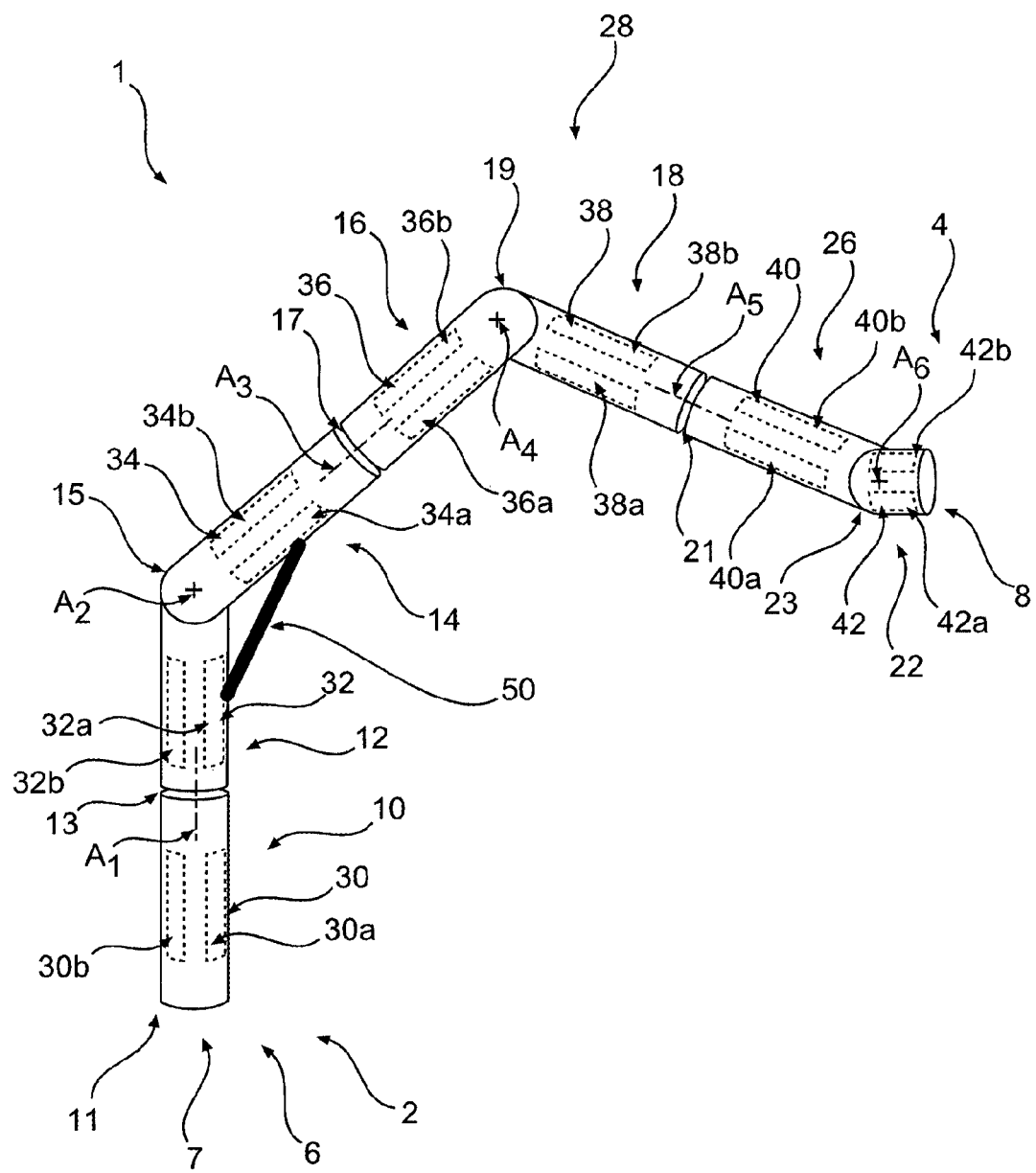
FIG. 1 shows a side view of a holding arm, in which the contacting device can be seen.

FIG. 1 shows a holding arm 1 for medical purposes, in particular for holding a surgical mechatronic assistance system and/or a surgical instrument. Holding arm 1 has a proximal end 2 and a distal end 4. At the proximal end 2, a first interface 6 and a mechanical interface 7 are formed, which are described in greater detail with reference to FIGS. 6 and 8. Interface 7 is used to attach holding arm 1 to a base, such as an operating table. Interface 7 is used to transfer energy and to couple holding arm 1 to an external control unit (cf. FIG. 5). At the distal end 4, a second interface 8 is provided via which it is possible to couple a mechatronic assistance system and/or a surgical instrument, such as a manipulator, to holding arm 1. A manipulator for holding and manipulating an endoscope is preferably disposed here.

Figure 7:
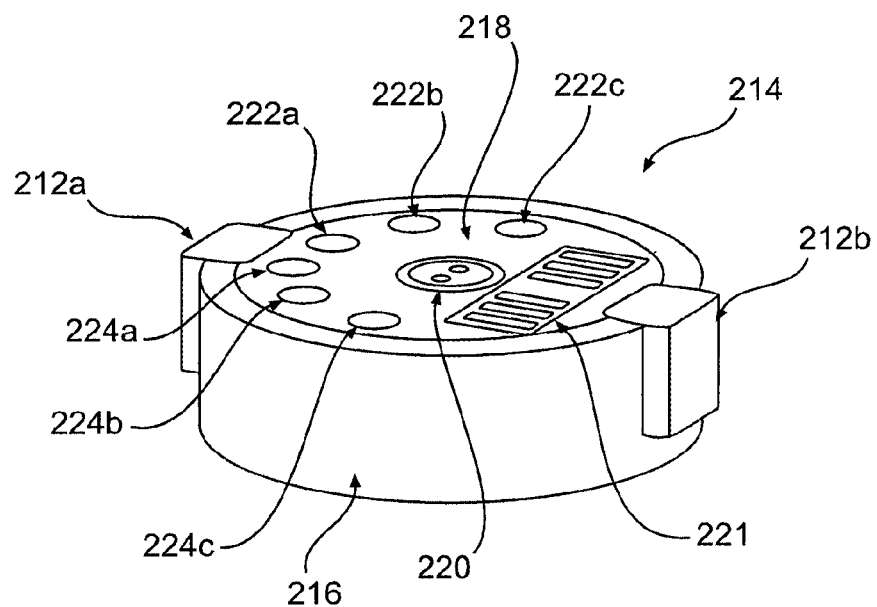
FIG. 7 shows a perspective view of an external energy storage unit.

The holding arm 1 according to FIG. 1 has seven arm segments 10, 12, 14, 16, 18, 20, 22, each of which is substantially rod-shaped and all of which, except for the last arm segment 22, are of substantially the same length. The seven arm segments 10, 12, 14, 16, 18, 20, 22 are each coupled to one another by joints 11, 13, 15, 17, 19, 21, 23, the zero-th joint 11 coupling holding arm 1 to the base (not shown in FIG. 1, see FIG. 7). In this embodiment, joints 13, 15, 17, 19, 21, 23 are all in the form of rotary joints each having one degree of freedom. According to this embodiment, the zero-th joint 11 is associated with the zero-th segment 10, the first joint 13 with the first arm segment 12, the second joint 15 with the second arm segment 14, the third joint 17 with the third arm segment 16, the fourth joint 19 with the fourth arm segment 18, the fifth joint 21 is associated with the fifth arm segment 20, and the sixth joint 23 is associated with the sixth arm segment 22. Joint 11 is designed as a translational joint, so that arm segment 10 can be extended telescopically in order to adjust the height of holding arm 1, as will be described later with reference to FIG. 8. Joints 13, 15, 17, 19, 21, 23 have respective pivot axes $A_1, A_2, A_3, A_4, A_5, A_6$, with respectively adjacent joints having pivot axes that are perpendicular to each other. This allows simple positioning of distal end 4 in space.

Holding arm 1 according to FIG. 1 also includes an operating unit 28. By means of the operating unit 28, holding arm 1 can be brought into a desired pose, the operating unit 28 being adapted to release the associated joint upon contact between an operator and one of the seven arm segments. For that purpose, the operating unit 28 according to this embodiment has seven contact areas 30, 32, 34, 36, 38, 40, 42, with one contacting device 30, 32, 34, 36, 38, 40, 42 being arranged on each arm segment 10, 12, 14, 16, 18, 20, 22. A zero-th contacting device 30 is thus arranged on the zero-th arm segment 10, a first contacting device 32 on the first arm segment 12, a second contacting device 34 on the second arm segment 14, a third contacting device 36 on the third arm segment 16, a fourth contacting device 38 on the fourth arm segment 18, a fifth contacting device 40 on the fifth arm segment 20 and a sixth contacting device 42 is arranged on the sixth arm segment 22.

According to this embodiment, each contacting device 30, 32, 34, 36, 38, 40, 42 also has two contact elements 30a, 30b, 32a, 32b, 34a, 34b, 36a, 36b, 38a, 38b, 40a, 40b, 42a, 42b arranged substantially opposite one another. Contacting devices 30, 32, 34, 36, 38, 40, 42 are used to detect contact between an operator and the respective arm segment 10, 12, 14, 16, 18, 20, 22. When gripping an arm segment 10, 12, 14, 16, 18, 20, 22, the operator comes into contact with the two contact elements 30a, 30b-42a, 42b, and the associated joint is released only when there is contact with both the contact elements 30a, 30b-42a, 42b of a contacting device 30-42. This means that, when the first arm segment 12 is gripped and the contact is made simultaneously with the two contact elements 32a, 32b, the first joint 13 is released by the operating unit 28. In this way, it is possible for the operator to pivot holding arm 1, or arm segments 12-22, about axis $A_1$. When one or both of the two contact elements 32a, 32b is let go of, joint 13 is locked again, and pivoting about axis $A_1$ is no longer possible. If only one of the two contact elements 32a, 32b is inadvertently touched, for example by an arm or elbow of the operator, joint 13 is not released and holding arm 1 remains in the locked state and keeps its pose.

The same applies to the second arm segment 14. In this case also, the second contacting device 34 has two contact elements 34a, 34b which are provided substantially opposite one another on the outer circumference of arm segment 14. When this arm segment 14 is gripped and contact is made with both the contact elements 34a, 34b, this contact is detected by the operating unit 28 and joint 15 associated with arm segment 14 is released. Pivoting about axis $A_2$ is now possible, so distal end 4, in FIG. 1, can be pivoted upwards or downwards. At the same time, all the other joints 13, 17, 19, 21, 23 remain locked, so no movement in them takes place.

For that purpose, operating unit 28 may have a controller or a microprocessor which is adapted to detect contact between contact elements 30a, 30b-42a, 42b and to transmit it in the form of electrical signals.

According to this embodiment, contacting device 30, or contact elements 30a, 30b-42a, 42b, are in the form of touch-sensitive sensors and detect the pressure of contact between the operator and the respective contact element 30a, 30b-42a, 42b. Contact elements 30a, 30b-42a, 42b are preferably provided in the form of capacitive touch-sensitive sensors.

With holding arm 1 shown here, it is also possible for an operator to grip two arm segments simultaneously, for example arm segment 14 and arm segment 18, and thus to contact simultaneously contact elements 34a, 34b and 38a, 38b. Joints 15 and 19 are released as a result, and it is possible to pivot them about axis A2 and also about axis A4. When joints are simultaneously released in this manner, it is possible for arm segments 18 and 20 to keep their angular orientation in space, while only arm segments 34, 36 are pivoted. This means that a translational movement of the distal end 4 is also possible. In one preferred configuration of the holding arm, it is not joints 15 and 19 that are released when two arm segments are contacted simultaneously in this example with arm segments 14 and 18, but all the joints between said arm segments 14 and 18, i.e. joints 17 and 19 in this embodiment. Joint 15 remains locked. The pose of holding arm 1 can now be changed in such a way that rotation about axis A3 and axis A4 is possible. This is a particularly intuitive way of operating the holding arm. Joints 15, 17, 19 and 21 are released accordingly, for example when there is contact between the operator and holding arm segments 12 and 20.

It can also be seen in FIG. 1 that holding arm 1 has a weight compensation unit 50. In this embodiment, the weight compensation unit 50 has a gas spring element which is coupled to arm segment 14 and arm segment 12. Alternatively, the weight compensation unit 50 may also have a cable pull and/or a equilibrated counterweight. In the case of holding arm 1 as shown in FIG. 1, the strongest torque is exerted on joint 15 about its rotational axis A2. It is therefore preferred that precisely that joint 15 be supported by means of the weight compensation unit 50. Thus, when joint 15 is released by contacting arm segment 14, a weight acting upon arm segment 14 due to the other arm segments 16, 18, 20, 22 and a manipulator disposed at interface 8, is supported by the weight compensation unit 50 so that the distal end 4 does not "sag" immediately when segment 14 is gripped.

Holding arm 1 (cf. FIG. 2) has a recognition unit 52 for recognizing an assistance system which is coupled to second interface 8, said operating unit 28 being adapted to release or to lock joints 11, 13, 15, 17, 19, 21, 23, depending on the assistance system which is coupled to the second interface 8. Such a recognition unit 52 preferably has a barcode scanner, a QR code scanner or an RFID scanner. An assistance system coupled to second interface 8 is preferably provided with a respective barcode, QR code or RFID chip containing an identifier for the assistance system and preferably information about said system. By this means, holding arm 1 is able to recognize which assistance system is coupled to second interface 8 and is thus able to partially or completely prevent the release of certain joints 11, 13, 15, 17, 19, 21, 23. An endoscope, for example, is disposed at second interface 8. The RFID chip of the endoscope contains information about said endoscope, such as the geometrical dimensions of the endoscope. This information is recognized by the recognition unit and is passed on to the operating unit 28 of holding arm 1 and/or to the external control unit. The operating unit 28 is configured to prevent such poses of holding arm 1 in which the endoscope would collide with the holding arm. The operating unit 28 may also be additionally configured to prevent such positions of holding arm 1 in which the endoscope would collide, for example, with an operating table or with other objects.

Figure 2:
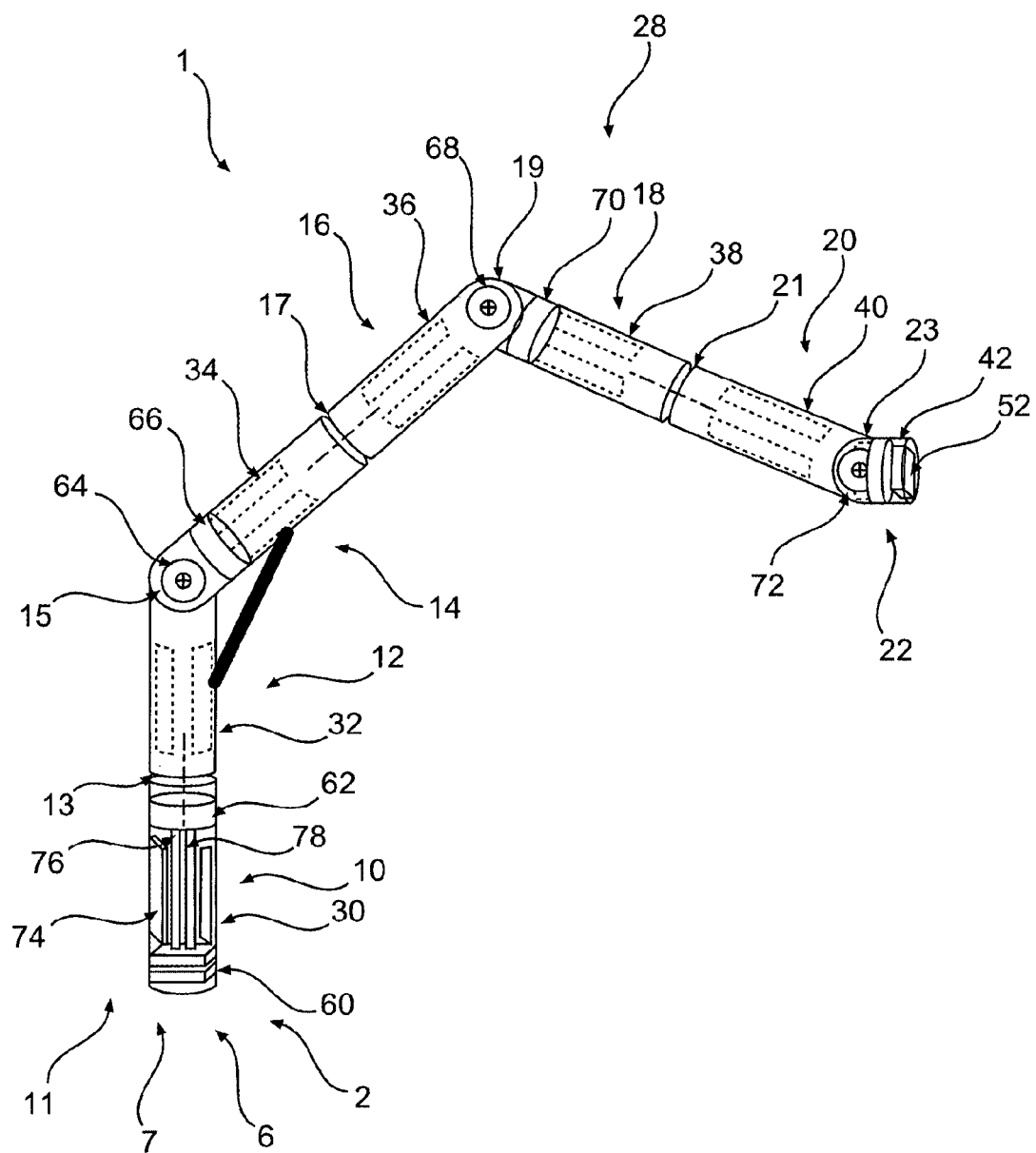
FIG. 2 shows a partly cutaway view of the holding arm shown in FIG. 1.

In addition to the elements of holding arm 1 already shown in FIG. 1, FIG. 2 shows brakes 60, 62, 64, 66, 68, 70, 72, by means of which joints 11, 13, 15, 17, 19, 21, 23 can be released and locked. Identical and similar elements are marked with the same reference signs as in FIG. 1, and reference is made in that respect to the entire description above. Although reference signs are not shown in FIG. 2 at the contact elements of contacting devices 30, 32, 34, 36, 38, 40, 42, for the sake of clarity, they are nevertheless present, as can be seen by comparing FIGS. 1 and 2.

A brake 60, 62, 64, 66, 68, 70, 72 is associated with each joint 11, 13, 15, 17, 19, 21, 23. Brake 60 is associated with joint 11, brake 62 with joint 13, brake 64 with joint 15, brake 66 with joint 17, brake 68 with joint 19, brake 70 with joint 21 and brake 72 with joint 23. All the brakes 60-72 are provided in the form of electromagnetic brakes and each comprise a permanent magnet which biases the brake into the locked state when no current is being supplied. The permanent magnet is designed in such a way that it can brake the respective joint on its own and so that the pose of holding arm 1 is held. In the zero-th arm segment 10, an electronic control unit 74 is provided. The latter is coupled via a bus system 76 (only shown in arm segment 10 in FIG. 2; cf. FIGS. 3 and 4) to all the contacting devices 30-42 of operating unit 28 and to all the brakes 60-72. In order to supply energy to brakes 60-72 and to contacting devices 30-42, an energy supply line 78 is also provided, which can be coupled to an energy source via interface 6 at the proximal end 2 of holding arm 1.

Figure 3:
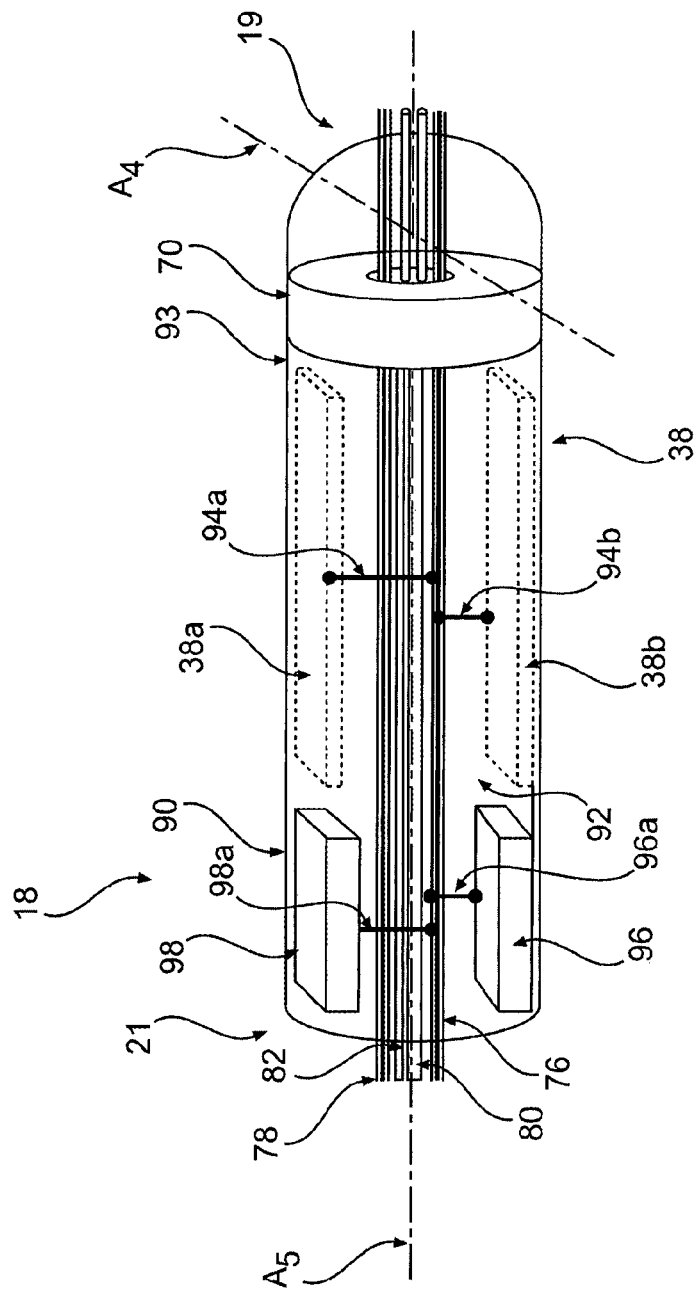
FIG. 3 shows a schematic view of the fourth arm segment.
Figure 4:
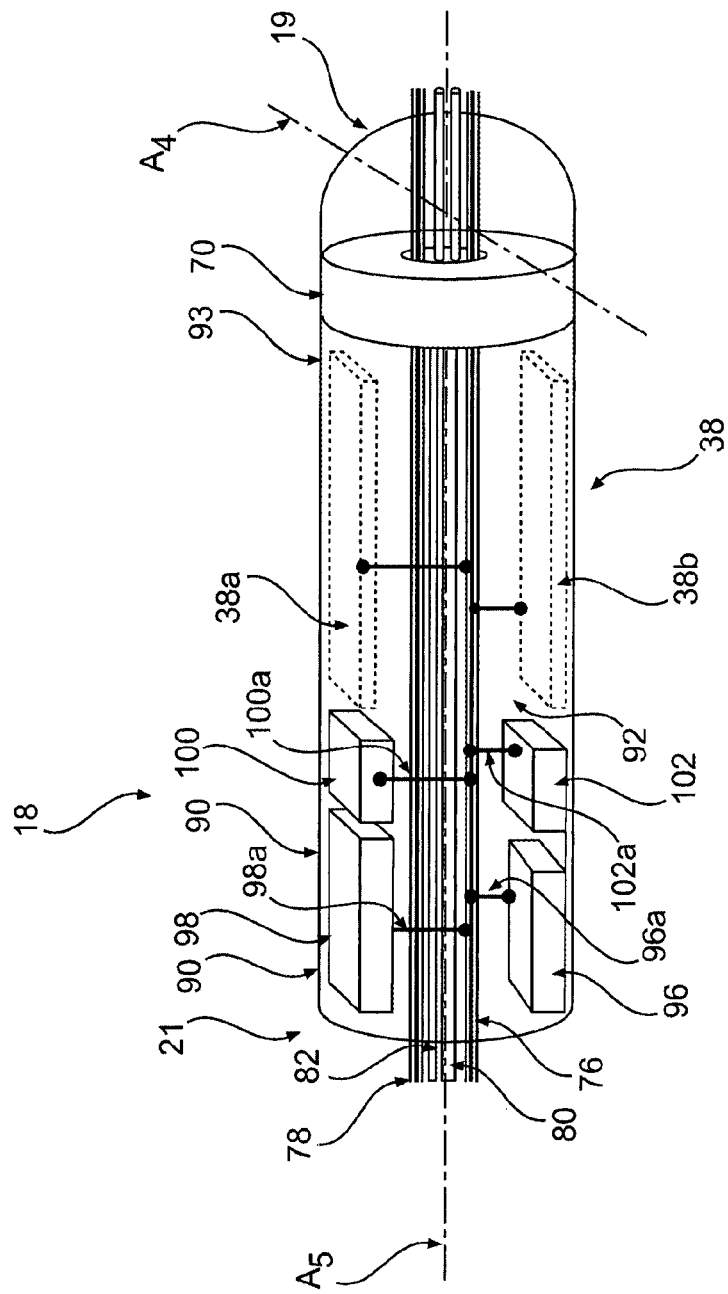
FIG. 4 shows another schematic view of the fourth arm segment.

FIGS. 3 and 4 show two different embodiments of an arm segment, with the fourth arm segment 18 being shown by way of example in FIGS. 3 and 4. It should be realized that the other arm segments 10, 12, 14, 16, 20, 22 may be configured the same way.

Arm segment 18 has an arm segment body 90 (not shown in FIGS. 1 and 2; it should be understood that each arm segment 10-22 has such an arm segment body), which according to FIGS. 3 and 4 is substantially rod-shaped and substantially cylindrical. Arm segment body 90 has a hollow space 92 inside, in which various elements such as brake 70 are arranged. Joints 19, 21 and the two pivot axes $A_4$, $A_5$ of joints 19, 21, which interact with holding arm segment 18, are shown schematically in FIGS. 3 and 4. Joint 19 is associated with holding arm segment 18 (cf. the description above referring to FIGS. 1 and 2). Arm segment body 90 has an outer surface 93 which is substantially cylindrical. Arm segment body 90 is made, for example, of a metal such as aluminum or titanium, an aluminum- or titanium-based alloy, or a composite fiber material such as GRP or CFRP, and is preferably of lightweight construction.

According to FIGS. 3 and 4, arm segment 18 has a contacting device 38, which is part of the operating unit 28 (cf. FIGS. 1 and 2). The contacting device 38 has two contact elements 38a, 38b, which are provided in the form of touch-sensitive sensors and which are arranged flush with the outer surface 93 of arm segment 18. The two contact elements 38a, 38b are arranged substantially opposite one other relative to axis $A_5$, so that an operator comes into contact with both the contact elements 38a, 38b when gripping arm segment 18, as described above.

The two contact elements 38a, 38b are coupled by means of lines 94a, 94b to bus system 76. Contact elements 38a, 38b are coupled via bus system 76 to the electronic control unit 74 (cf. FIG. 2) and via the latter to brake 70, so that brake 70 is released by the operating unit 28 when an operator comes into contact with contact elements 38a, 38b.

In addition to bus system 76, an energy transmission system 78 and a cable duct 80 and a working channel 82 are arranged inside arm segment body 90. By means of energy transmission system 78, contact elements 38a, 38b and brake 70 are connected to an energy supply.

Alternatively or additionally, an electronics module 96 which is coupled to bus system 76 via a line 96a is disposed inside each arm segment. In such a case, contact elements 38a, 38b, which are connected via line 94a, 94b to data bus 76, interact only with electronics module 96, which converts the contact detected by contact elements 38a, 38b into a control signal for brake 70 and sends said control signal via bus system 76 to brake 70 in order to release joint 19. If such an electronics module 96 is disposed inside each arm segment, holding arm 1 has a substantially modular structure, and the individual arm segments 10-22 are independent of the electronic control unit 74 which is disposed in proximal arm segment 10.

Cable duct 80 is used to guide cables running from the proximal end 2 to the distal end 4 to supply interface 8, in particular. Working channel 82 is used to receives tubes or waveguides and the like as may be required by that particular kind of manipulator disposed at interface 8. If, for example, an endoscope is disposed at interface 8, a waveguide which can transmit an image recorded by an endoscopic camera is preferably guided through working channel 82. Working channel 82 is thus used to receive transmission means appropriate to the particular field of application.

There is also a sensor 98 disposed inside arm segment 18. A sensor is preferably disposed in each arm segment 10-22, and it should be understood that the sensors in arm segments 10, 12, 14, 16, 20 and 22 may be configured in the same way as sensor 98 in arm segment 18. Sensor 98 is preferably provided in the form of an acceleration sensor. By providing such an acceleration sensor in each arm segment, it is possible to determine the pose of holding arm 1 at any time. For that purpose, sensor 98 is coupled via line 98a to data bus 76, so that the data captured by sensor 98 are transmitted to the electronic control unit 74, which then determines the pose of holding arm 1 from all the sensor data from all the arm segments. By providing such a sensor 98, it is also possible to determine the absolute and relative position of an end effector or manipulator disposed at interface 8. If holding arm 1 is attached to an operating table, it is also possible to detect any movement of the operating table. If all the sensors in all the arm segments detect a movement in the same direction, this is an indication that the entire holding arm 1 has been moved while keeping its pose, for example by the operating table or a plate of the operating table having been rotated or displaced relative to a pillar of the operating table. Such movement can also be detected by use of sensors 98. External impulses, such as jolts against holding arm 1, can also be detected.

According to FIG. 4, an accumulator element 100 and a power generation unit 102 are additionally provided in the arm segment 18 of FIG. 3. The accumulator element is used to store electrical energy, so that sensors provided in the specific arm segment can be supplied with current even when disconnected from the power grid. This is necessary, in particular, whenever bump sensors of a camera or the like are provided, for example, which have to function, even when the holding arm is in an idle state, in order to detect possible damage to holding arm 1. Power generation unit 102 is used to provide energy for a laser, an ultrasonic device, or the like, which is coupled to the holding arm. Additionally or alternatively, power generation unit 102 may also have a device for supplying accumulator element 100, for example an energy harvesting element which converts kinetic energy, or energy resulting from a magnetic field, for example inductively, into electrical voltage for accumulator element 100.

Figure 5:
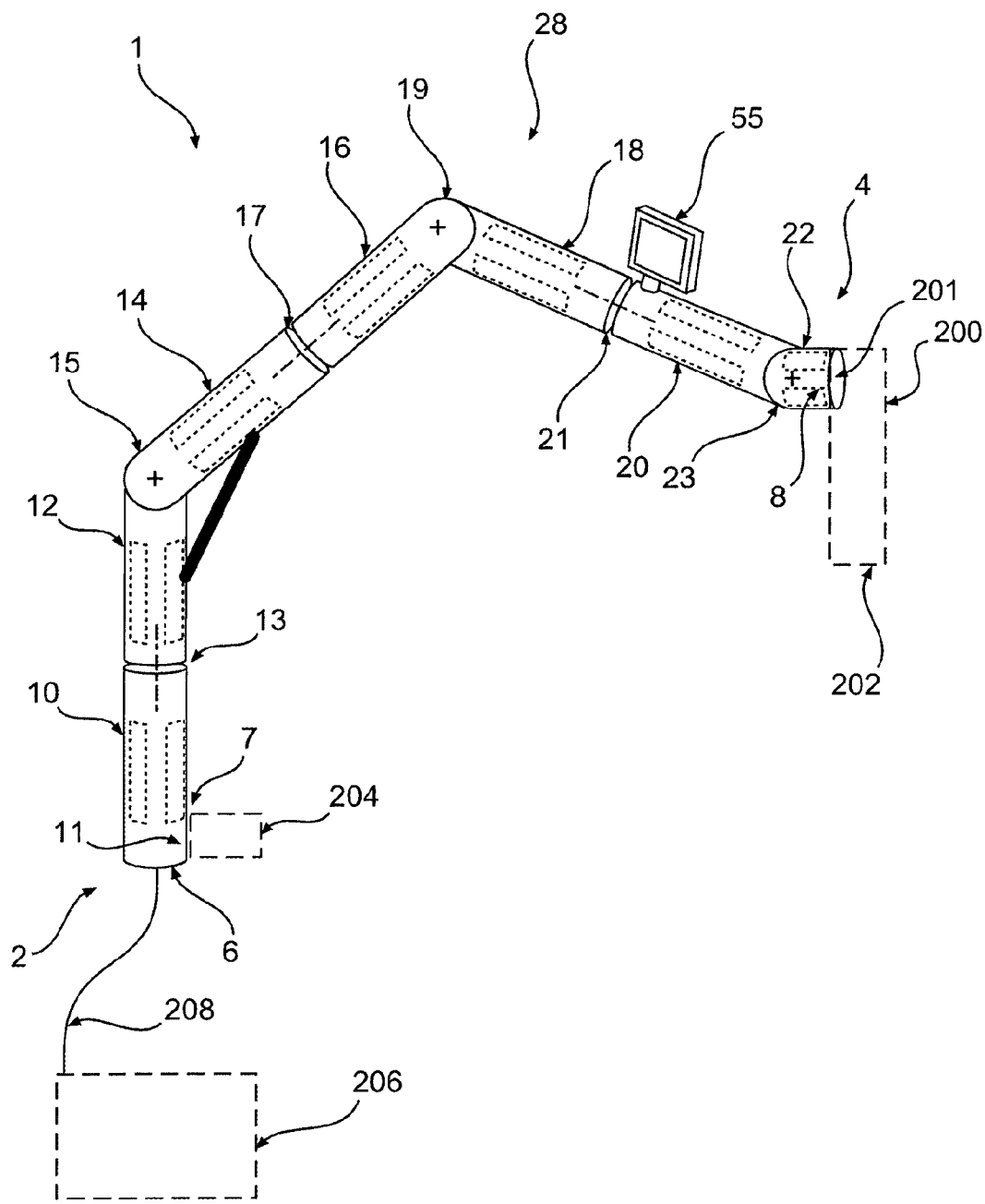
FIG. 5 shows the holding arm from FIG. 1, coupled to an external control unit.
Figure 6:
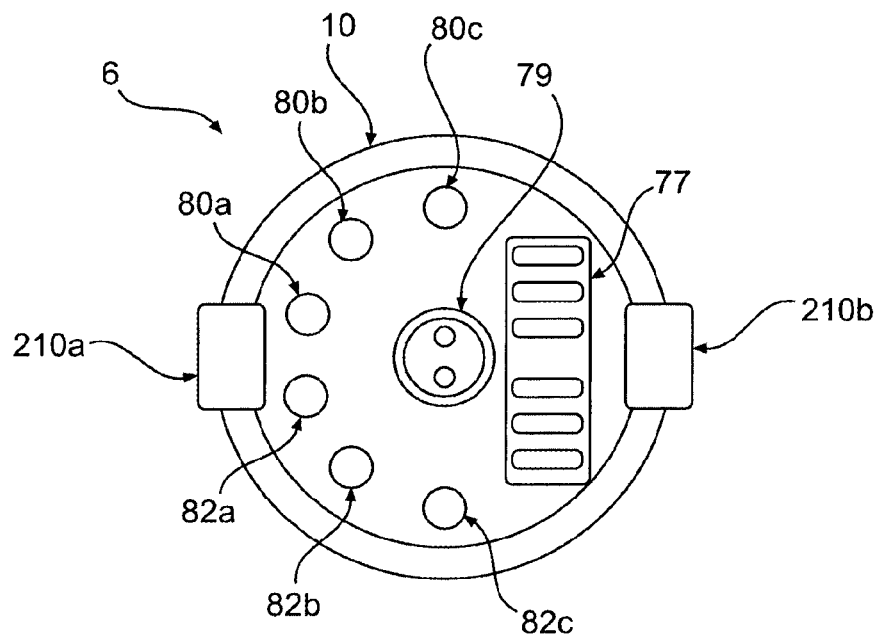
FIG. 6 shows a plan view of the interface at the proximal end of the holding arm.

FIG. 5 illustrates holding arm 1 once again, as already described with reference to FIGS. 1 and 2. In FIG. 5, holding arm 1 is shown integrated within a system. At distal end 4, by use of interface 8, a surgical mechatronic assistance system 200 is arranged which is coupled to interface 8 via an interface 201. Both the surgical mechatronic assistance system 200 and interface 201 are shown only schematically in FIG. 5. It should be understood that the surgical mechatronic assistance system 200 may be provided in the form of an endoscope, for example, or as a laparoscope or the like. Assistance system 200 has a working section 202, which can be the tip of the endoscope, for example. At proximal end 2, holding arm 1 according to FIG. 5 is coupled to a base 204 via mechanical interface 7. Base 204 is shown here likewise in schematic form only. It may be provided in the form of a standard rail of an operating table, for example.

According to this embodiment, first interface 6 is coupled to an external control unit 206. For that purpose, interface 6 is connected by means of a cable 208 to external control unit 206. According to this embodiment, external control unit 206 is provided in the form of an OP system comprising, for example, a conventional computer and an input-output interface for operating the OP system. The OP system preferably has software components which are configured to store and process data transferred from holding arm 1 at interface 6.

Depending on the configuration of interface 6, the interface may communicate wirelessly with OP system 206, for example via Bluetooth®, Wi-Fi® or similar.

According to this embodiment, holding arm 1 also has a display 55 which is provided in the form of an LCD display in this embodiment. Display 55 is connected to a control unit and displays representations of data which are transferred at first interface 6 or second interface 8. The display displays, for example, the weight of an assistance system 200 which is coupled to interface 8. Alternatively, a representation of the pose of the holding arm, with the respective loads on individual joints, is displayed on the display. Other possibilities are conceivable here. It is also conceivable that warning messages are displayed here.

Interface 6 (see FIG. 6) has a connector 77 for bus system 76. Data outputted by sensors (cf. FIGS. 3 and 4) and by contact elements (cf. FIGS. 2-4) to bus system 76 can be transferred via said connector 77 to external control unit 206. For that purpose, connector 77 may be configured as a USB interface, an RS-232 interface, a Bluetooth® interface, a Wi-Fi® interface or the like. A connector 79 for transmitting electrical energy is also provided in the middle of interface 6. By means of this connector 79, holding arm 1 can be coupled to an energy source, for example to the power grid. Three outlets 80a, 80b, 80c of cable duct 80 (cf. the above description referring to FIGS. 2, 3 and 4) are also provided at interface 6. Cables fed through cable ducts 80 can be accessed via these outlets 80a, 80b, 80c. Three outlets 82a, 82b, 82c of working channel 82 are also provided in interface 6. Working channel 82 can be accessed via outlets 82a, 82b, 82c. It is thus possible, for example, for a tube to be guided through outlet 82b into working channel 82 by means of interface 6 and guided through working channel 82 as far as distal interface 8 (cf. FIG. 10).

On a peripheral region of arm segment 10, first mechanical couplings 210a, 210b are provided in the region of interface 6. First couplings 210a, 210b match second couplings 212a, 212b of an external energy storage unit 214 (see FIG. 7). External energy storage unit 214 has a housing 216 which is so designed that it can be joined proximally to arm segment 10. External energy storage unit 214 has cells inside it for storing electrical energy (not shown in FIG. 7). External energy storage unit 214 has an interface 218 which matches interface 6 of holding arm 1. Interface 218 has a connector 220 by means of which the electrical energy stored in external energy storage unit 214 can be transferred to holding arm 1 via connector 79 of interface 6. Interface 218 also has a connector 221 which matches interface 77, for passing on signals of bus system 76. The external energy storage unit 214 also has through passages 222a, b, c, 224a, b, c, corresponding to outlets 80a, b, c and 82a, b, c of interface 6, so that cables fed through cable duct 80 can also be guided through energy storage unit 214 and so that outlets 82a, 82b, 82c of working channel 82 are accessible at the energy storage unit 214.

Figure 8:
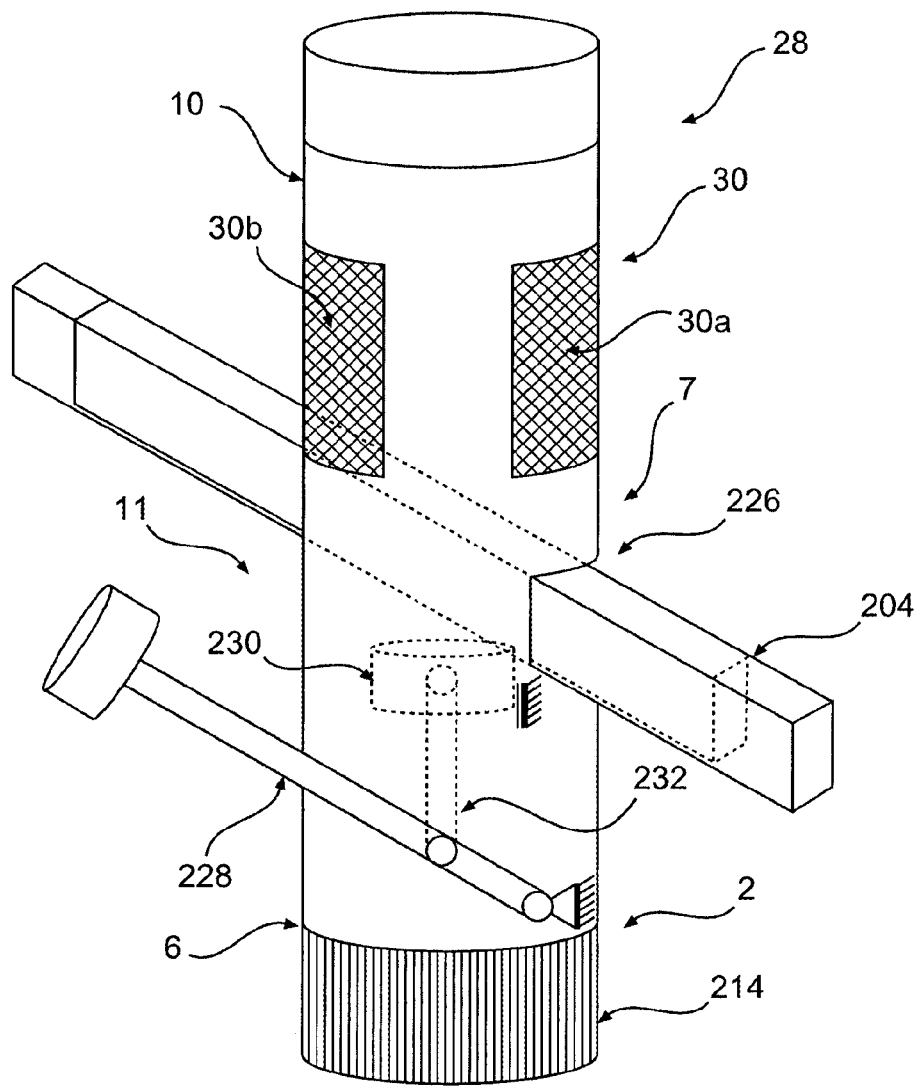
FIG. 8 shows a perspective schematic view of the first arm segment, with a mechanical interface for coupling the holding arm to a standard rail of an operating table.

FIG. 8 illustrates arm segment 10 forming the proximal end 2 of the holding arm, and in particular mechanical interface 7. The external energy storage unit 214 (cf. FIG. 7) is arranged at the first interface 6, so holding arm 1 according to this embodiment (FIG. 8) can be operated autonomously, without having to be connected to an external energy source. A connection to a control unit 206 may be provided nevertheless, and is preferred. Arm segment 10 has a contacting device 30, which has two contacting elements 30a, 30b hat (see also FIG. 2). According to this embodiment, interface 7 is provided in the form of a recess 226 which matches the outer contour of base 204, which is provided here in the form of a standard rail of an operating table. Base 204 can be guided in recess 226, and mechanical clamping device 228 are provided on arm segment 10 for clamping the arm segment 10 against base 204. The clamping device has a linearly guided clamp member 230 which can be driven by means of a lever 224 via a rod 232. Joint 11, which can be released via the contacting device 30 of the operating unit 28, is therefore designed as a translational joint 11. The operating unit is coupled to lever 228 via an electrical adjusting device which is not shown in FIG. 8, so that clamping device 230 can be disengaged from base 204.

Figure 9:
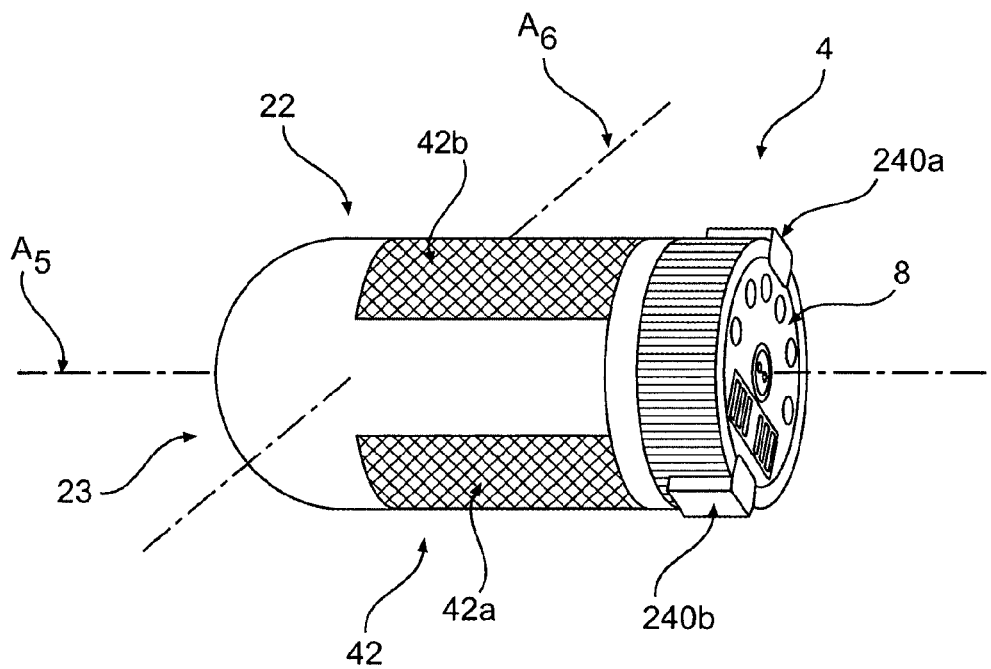
FIG. 9 shows a perspective view of the seventh arm segment, including the interface at the distal end.
Figure 10:
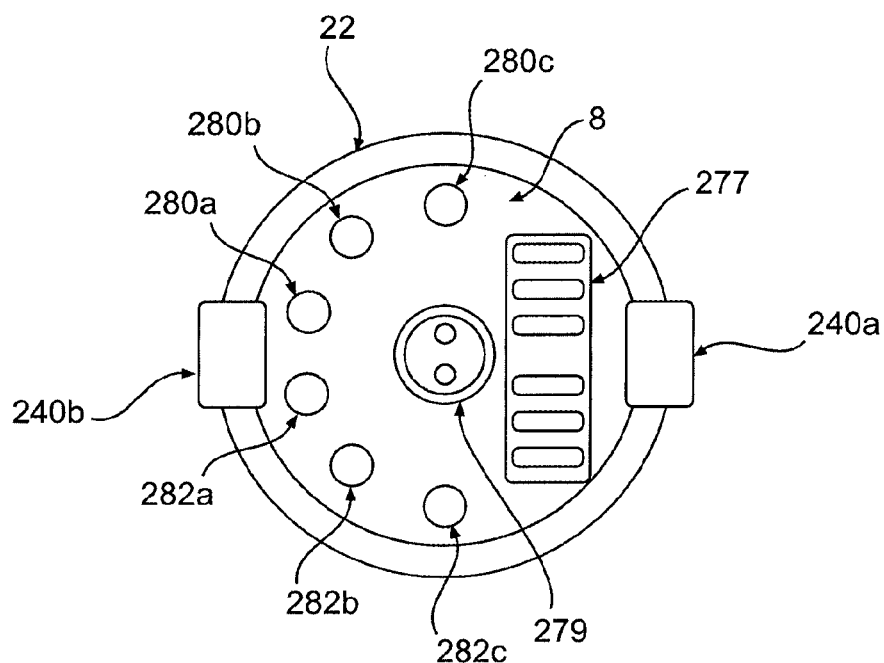
FIG. 10 shows a plan view of the interface at the distal end of the holding arm.

Finally, FIGS. 9 and 10 illustrate the second interface 8 at distal end 2 of holding arm 1. Whereas FIG. 9 shows interface 8 in a perspective view that includes arm segment 22, FIG. 10 shows interface 8 in a frontal view.

Interface 8 is configured so that it substantially matches interface 6. On lateral portions of the latter, on arm segment 22, two safety elements 240a, 240b are arranged. By means of the safety elements, it is possible to determine whether an assistance system 200 coupled to interface 8 (see FIG. 5) is correctly coupled to interface 8. Safety elements 240a, 240b are used simultaneously as a mechanical coupling for coupling mechanically to assistance system 200, for example by a clamping or latching mechanism.

A connector 277, which matches connector 77 of interface 6, is also disposed at interface 8. Connector 277 is coupled to bus system 76, so that data and signals from connector 77 are transferred via bus system 76 to connector 77, and vice versa. A connector 279 is likewise provided at interface 8, for transferring electrical energy from interface 8 to assistance system 200. Connector 279 matches connector 79 of interface 6, and the two connectors 279 and 79 are coupled by means of the transmission unit 78 for transmitting electrical energy between said two connectors 79, 279.

Outlets 280a, 280b, 280c of cable duct 80 are also provided at interface 8, so that cables fed through said duct can be accessed at interface 8. The same applies for working channel 82, three outlets 282a, 282b, 282c from which are provide at interface 8. An assistance system 200 can be coupled advantageously via said interface 8 to holding arm 1, without additional transmission means or wiring having to be provided on holding arm 1.

Figure 11A:
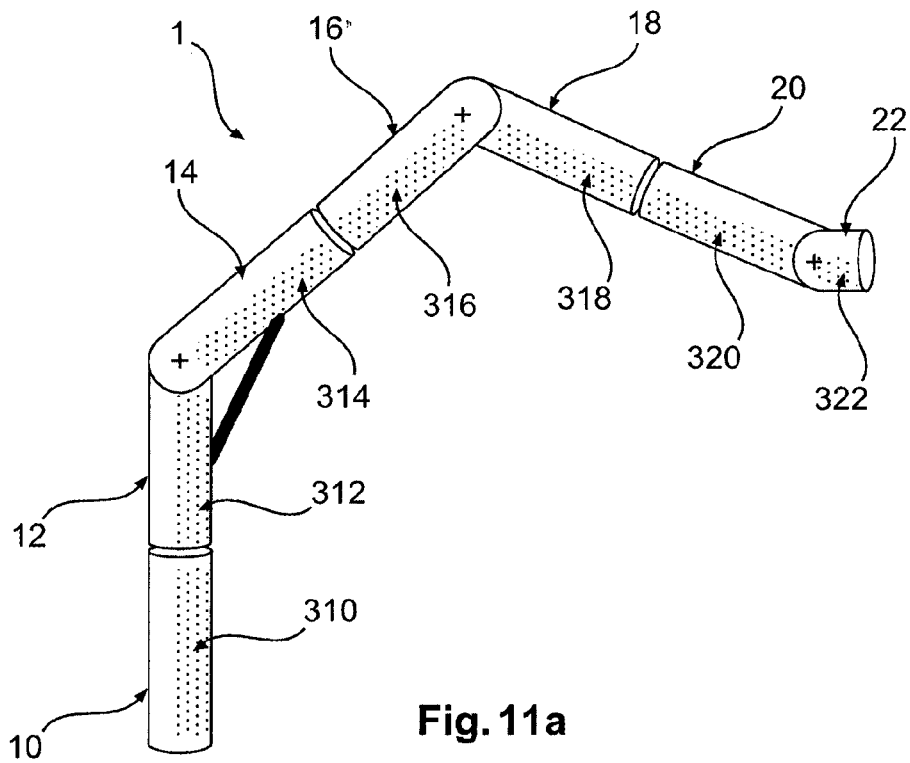
FIG. 11a shows an embodiment of the holding arm with a partly structured surface.
Figure 11B:
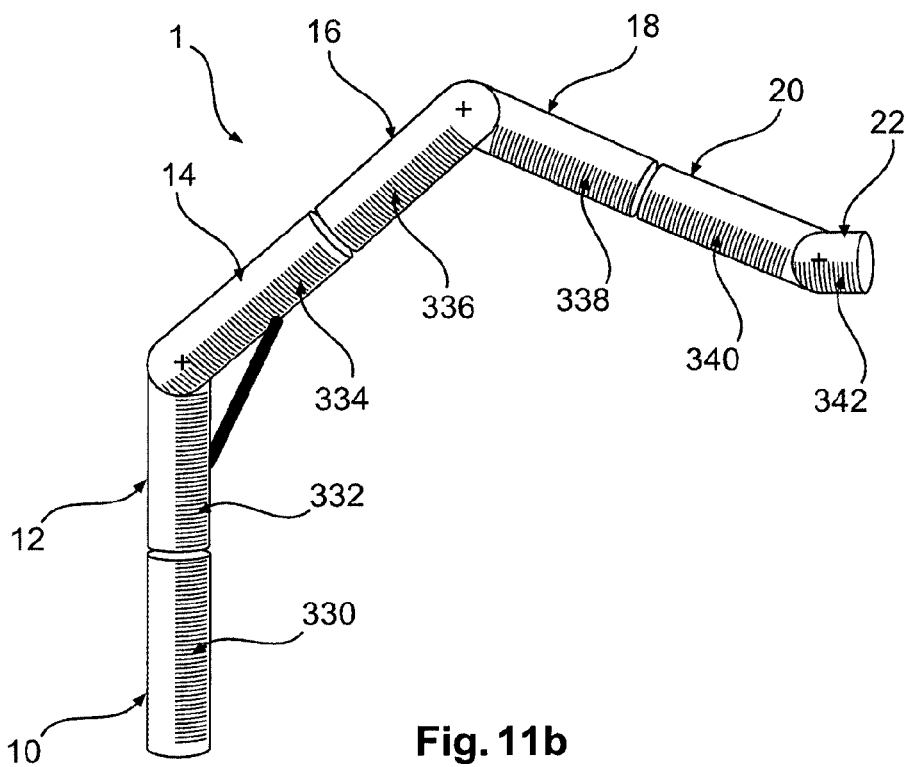
FIG. 11b shows an embodiment of a holding arm with a partly colored surface.

FIGS. 11a and 11b show two further embodiments of holding arm 1 which are substantially similar in configuration to the first embodiment according to FIGS. 1 and 2. In addition to the features described therein, the holding arms according to FIGS. 11a, 11b each have orientation indicators 310, 312, 314, 316, 318, 320, 322, 330, 332, 334, 336, 338, 340, 342. According to FIG. 11a, orientation indicators 310, 312, 314, 316, 318, 320, 322 are provided in the form of a surface structure. The individual arm segments 10, 12, 14, 16, 18, 20, 22, which are substantially cylindrical in shape, have structuring along approximately half the outer cylindrical surface. According to this embodiment, the structuring is arranged in such a way that orientation indicators 310, 312, 314, 316, 318, 320, 322 of holding arm 1 are oriented, in relation to the operating area, in a basic pose of holding arm 1 as shown in FIG. 11a. By means of the structuring, which acts as orientation indicators 310, 312, 314, 316, 318, 320, 322, an operator is able to establish by tactile means whether an arm segment 10, 12, 14, 16, 18, 20, 22 is oriented in its basic pose, or whether the holding arm is inverted, that is to say oriented with the structured surface facing away from the operating area. This may be important for weight compensation.

Alternatively, FIG. 11b shows an embodiment in which orientation indicators 330, 332, 334, 336, 338, 340, 342 are provided in the form of colored markings. A color gradient which can be visually perceived by an operator is provided on the side of arm segments 10, 12, 14, 16, 18, 20, 22 facing the operating area. By this means, the operator can directly recognize the orientation of holding arm 1.

Figure 12:
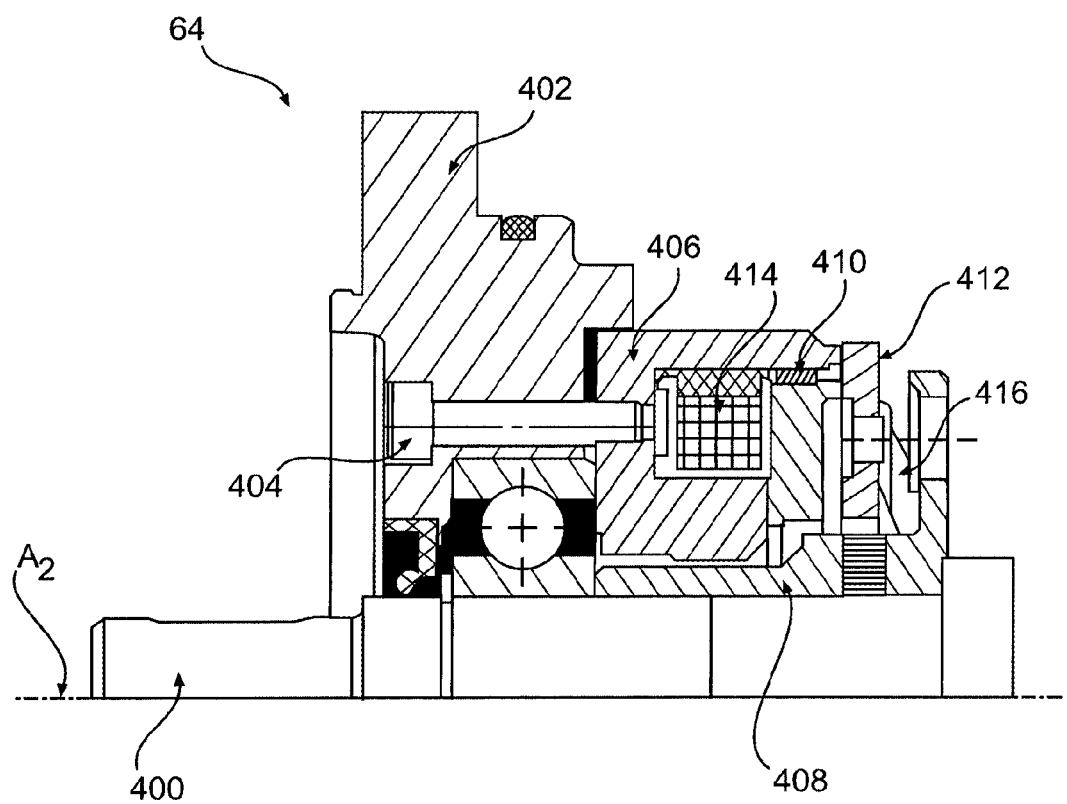
FIG. 12 shows a partial section through a brake in a joint of the holding arm.

FIG. 12 shows, in schematic form, a partial cross-sectional view of an example of a brake as provided, for example, as brake 64 in joint 15. It should be understood that the other brakes 60, 62, 66, 68, 70, 72 may also be configured the same way. According to this embodiment (FIG. 12), brake 74 is in the form of an electromagnetic permanent magnet brake. A first joint element 400, provided here in the form of a shaft, is rigidly connected to arm segment 12, and a second joint element 402 is rigidly connected to arm segment 14. It should be understood that this can also be exactly the other way round. The second joint element 402 is securely coupled to a housing 406 of brake 64 by a screw 404. A flanged hub 408 is coupled appropriately securely to the first joint 400. A permanent magnet 410 is arranged inside housing 406 and is used to press an anchor 412, which is securely connected to flange 408, against housing 406. This causes static friction, which acts as a braking force. Inside housing 406, there is also an exciter coil 414 which, when supplied with current, produces a field that counteracts permanent magnet 410. By use of a spring element 416 which biases anchor 412 in a vented state, the latter is lifted from housing 406, thus venting brake 64. It is thus possible for the second joint element 402 to rotate about the first joint element 400, about axis A2.

Figure 13:
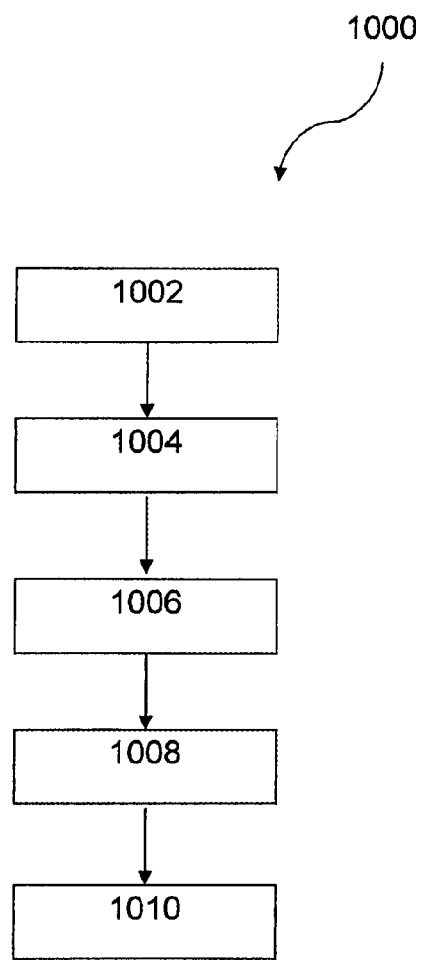
FIG. 13 shows a flow diagram of a method according to a first embodiment.

FIG. 13 shows a method 1000 for controlling a mechatronic assistance system 200 coupled to a holding arm 1 in accordance with a first embodiment. According to this embodiment, method 1000 comprises five steps which are performed successively or partly simultaneously. In the first step 1002, holding arm 1 is attached to a standard rail of an operating table and put into operation. For this purpose, the first interface 4 is connected to an OP system 206 (see also FIG. 5), so that data and electrical energy are transmitted to holding arm 1 at first interface 6. In step 1004, a mechatronic assistance system 200 is coupled to a second interface 8 of holding arm 1 at its distal end 4. Subsequent steps 1006-1010 are then performed preferably simultaneously. In step 1006, electrical energy and signals are transferred to the holding arm from first interface 6 of holding arm 1 at its proximal end. The data and electrical energy are transmitted from first interface 6 to second interface 8 by use of a transmission unit 76, 78 inside holding arm 1. At the second interface at the distal end, data and electrical energy are transmitted to the assistance system in step 1010, so that assistance system 200 can be operated.

Figure 14:
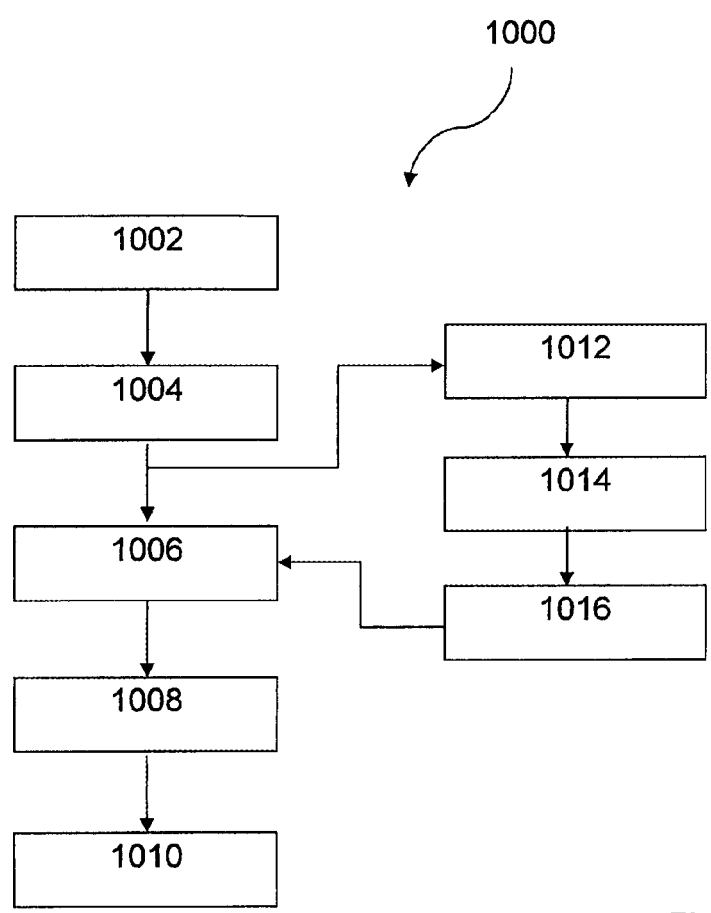
FIG. 14 shows a flow diagram of a method according to a second embodiment.

FIG. 14 shows another embodiment of method 1000. Steps 1002-1010 correspond to the embodiment according to FIG. 13 and in that respect reference is made to the entire description above. According to step 1004, there is a branch in this method (see FIG. 14) to step 1012. In step 1012, attitudes of joints of the holding arm are detected. In step 1014, a pose of the holding arm is determined using the detected attitudes of the joints. Data representing the specific pose are subsequently provided in step 1016, namely at the first interface 6, and are transmitted in step 1006. In this way, the pose of the holding arm can be transmitted at the first interface to an OP system, where they can then be used.

The other preferred embodiments of the method as described above are configured in a similar manner, wherein the respective steps can be performed substantially simultaneously and continuously.

The invention claimed is:

1. A holding arm for holding a surgical mechatronic assistance system or surgical instrument, the holding arm comprising:
    a proximal end for attaching the holding arm to a base and a distal end for receiving the surgical mechatronic assistance system or the surgical instrument;
    a first interface at the proximal end for connecting the holding arm to an energy source and to an external control unit for transmitting signals to and from the holding arm;
    a second interface at the distal end for coupling the holding arm to the surgical mechatronic assistance system or the surgical instrument to control the surgical mechatronic assistance system or the surgical instrument;
    a transmission unit connecting the first interface to the second interface to transmit energy and signals between the first and second interfaces;
    a recognition unit configured to recognize the surgical mechatronic assistance system or the surgical instrument coupled to the second interface;
    a first arm segment and a second arm segment, wherein the first arm segment is connected to a first joint and the second arm segment is connected to a second joint, wherein each of the first joint and the second joint is releasable and lockable based on a type of the surgical mechatronic assistance system or the surgical instrument coupled to the second interface;
    a switch adapted to release both the first joint and the second joint; and
    a first contacting device arranged on the first arm segment, wherein the first contacting device is adapted to release the first joint when a contact occurs between an operator and the first contacting device.

2. The holding arm according to claim 1, further comprising a second contacting device arranged on the second arm segment, wherein the second contacting device is adapted to release the second joint when a contact occurs between the operator and the second contacting device.

3. The holding arm according to claim 1, wherein the first contacting device has two contact elements arranged substantially opposite one another on the first arm segment.

4. The holding arm according to claim 3, wherein the two contact elements are pushbuttons or touch-sensitive sensors.

5. The holding arm according to claim 1, wherein the first joint comprises a first brake adapted to release and lock the first joint and the second joint comprises a second brake adapted to release and lock the second joint, and wherein the first brake is a first electromagnetic brake that is biased to maintain the first joint into a locked state when no current is being supplied and the second brake is a second electromagnetic brake that is biased to maintain the second joint into a locked state when no current is being supplied.

6. The holding arm according to claim 1, wherein the holding arm comprises seven arm segments including the first arm segment and the second arm segment and seven joints including the first joint and the second joint.

7. The holding arm according to claim 1, wherein the proximal end comprises a first mechanical coupling for releasably coupling the holding arm to a second corresponding coupling of an operating table.

8. The holding arm according to claim 1, wherein the distal end second interface comprises a mechatronic interface for coupling the surgical mechatronic assistance system or the surgical instrument.

9. The holding arm according to claim 1, wherein the first interface comprises a connector for an external accumulator.

10. The holding arm according to claim 1, wherein the transmission unit comprises a bus.

11. The holding arm according to claim 1, wherein the recognition unit comprises a camera configured to observe an operating area and coupled to the first interface to transfer image data.

12. The holding arm according to claim 1, further comprising a safety element at the second interface, wherein the safety element is configured to identify a faulty link between the surgical mechatronic assistance system or the surgical instrument and the second interface, and to lock all joints of the holding arm in response to identifying the faulty link between the surgical mechatronic assistance system or the surgical instrument and the second interface.

13. The holding arm according to claim 1, further comprising a display configured to display a representation of data transferred to the first or second interface.

14. The holding arm according to claim 1, further comprising an orientation sensor in at least one of the first joint or the second joint and configured to detect an attitude of the first joint or the second joint.

15. The holding arm according to claim 1, further comprising a torque sensor disposed in at least one of the first joint or the second joint and configured to detect a torque acting on said first joint or the second joint.

16. The holding arm according to claim 1, wherein at least one of the first arm segment or the second arm segment comprises a sensor configured to detect a position of said first arm segment or said second arm segment.

17. The holding arm of claim 1, wherein the switch is at the distal end of the holding arm or is a footswitch disposed at a distance from the holding arm.

18. The holding arm of claim 17, wherein the switch is adapted to release both the first joint and the second joint simultaneously.

19. A holding arm for holding a surgical mechatronic assistance system or surgical instrument, the holding arm comprising:
a proximal end for attaching the holding arm to a base and a distal end for receiving the surgical mechatronic assistance system or the surgical instrument;
a first arm segment and a second arm segment, wherein the first arm segment is connected to a first joint and the second arm segment is connected to a second joint, wherein each of the first joint and the second joint is releasable and lockable;
a first electromagnetic brake in the first joint that is adapted to release and lock the first joint, the first electromagnetic brake comprising a first permanent magnet, and the first electromagnetic brake being biased to maintain the first joint into a locked state when no current is being supplied;
a second electromagnetic brake in the second joint that is adapted to release and lock the second joint, the second electromagnetic brake comprising a second permanent magnet, and the second electromagnetic brake being biased to maintain the second joint into the locked state when no current is being supplied;
a switch adapted to release both the first joint and the second joint; and
a first contacting device arranged on the first arm segment, wherein the first contacting device is adapted to release the first joint when a contact occurs between an operator and the first contacting device.

20. The holding arm according to claim 19, further comprising a second contacting device arranged on the second arm segment, wherein the second contacting device is adapted to release the second joint when a contact occurs between the operator and the second contacting device.

21. The holding arm according to claim 19, wherein the first contacting device has two contact elements arranged substantially opposite one another on the first arm segment.

22. The holding arm according to claim 19, wherein the holding arm comprises seven arm segments including the first arm segment and the second arm segment and seven joints including the first joint and the second joint.

23. The holding arm according to claim 19, further comprising:
a first interface at the proximal end for connecting the holding arm to an energy source and to an external control unit for transmitting signals to and from the holding arm;
a second interface at the distal end for coupling the holding arm to the surgical mechatronic assistance system to control the surgical mechatronic assistance system; and
a transmission unit connecting the first interface to the second interface to transmit energy and signals between the first and second interfaces.

24. The holding arm according to claim 23, wherein the first interface comprises a connector for an external accumulator.

25. The holding arm according to claim 23, wherein the transmission unit comprises a bus.

26. The holding arm according to claim 23, further comprising a recognition unit configured to recognize the surgical mechatronic assistance system coupled to the second interface, wherein control of releasing or locking of the first and second joints is based on a type of the surgical mechatronic assistance system coupled to the second interface.

27. The holding arm according to claim 19, further comprising a torque sensor disposed in at least one of the first joint or the second joint and configured to detect a torque acting on said first joint or the second joint.

28. The holding arm according to claim 19, wherein at least one of the first arm segment or the second arm segment comprises a sensor configured to detect a position of said first arm segment or said second arm segment.

29. The holding arm of claim 19, wherein the switch is at the distal end of the holding arm or is a footswitch disposed at a distance from the holding arm, and wherein the switch is adapted to release both the first joint and the second joint simultaneously.

* * * * *